United States Patent
Peng et al.

(10) Patent No.: US 9,217,710 B2
(45) Date of Patent: Dec. 22, 2015

(54) METHOD OF SIMULTANEOUS FREQUENCY-SWEEPING LIFETIME MEASUREMENTS ON MULTIPLE EXCITATION WAVELENGTHS

(71) Applicant: The Arizona Board of Regents on behalf of the University of Arizona, Tucson, AZ (US)

(72) Inventors: Leilei Peng, Tucson, AZ (US); Ming Zhao, Tucson, AZ (US)

(73) Assignee: The Arizona Board of Regents on behalf of the University of Arizona, Tucson, AZ (US)

( * ) Notice: Subject to any disclaimer, the term of this patent is extended or adjusted under 35 U.S.C. 154(b) by 134 days.

(21) Appl. No.: 13/956,212

(22) Filed: Jul. 31, 2013

(65) Prior Publication Data

US 2015/0037877 A1 Feb. 5, 2015

(51) Int. Cl.
*G01N 21/64* (2006.01)
(52) U.S. Cl.
CPC ........ *G01N 21/6408* (2013.01); *G01N 21/6428* (2013.01); *G01N 2021/6421* (2013.01); *G01N 2021/6432* (2013.01); *G01N 2021/6441* (2013.01); *G01N 2201/10* (2013.01); *G01N 2201/126* (2013.01)
(58) Field of Classification Search
CPC .................. G01N 21/6408; G01N 2021/6419; G01N 2021/6421; G01N 21/6458; G01N 2201/10; G01N 21/6428; G01J 3/4406; G01J 3/0208; G01J 3/4535; G02B 21/002
USPC ...................................................... 250/459.1
See application file for complete search history.

(56) References Cited

U.S. PATENT DOCUMENTS

2007/0087445 A1* 4/2007 Tearney et al. ............... 436/172
2010/0059696 A1* 3/2010 Heintzmann et al. ......... 250/550
2011/0134436 A1* 6/2011 Podoleanu et al. ........... 356/512

OTHER PUBLICATIONS

H. J. Carlson and R. E. Campbell, "Genetically encoded FRET-based biosensors for multiparameter fluorescence imaging," Current Opinion in Biotechnology 20, 19 (2009).
M. Zhao, R. Huang, and L. Peng, "Optics InfoBase: Optics Express—Quantitative multi-color FRET measurements by Fourier lifetime excitation-emission matrix spectroscopy," Optics Express (2012) 26806-26827.
T. Forster, "Intermolecular energy migration and fluoroscence," Ann. Phys 2, 55-75 (1948).
L. Stryer, "Fluorescence energy transfer as a spectroscopic ruler," Annu. Rev. Biochem. 47, 819-846 (1978).

(Continued)

*Primary Examiner* — Marcus Taningco
(74) *Attorney, Agent, or Firm* — Davis Wright Tremaine LLP

(57) ABSTRACT

A fast fluorescence lifetime microscopic system images FRET between multiple labels in live cells and deep tissue, using a quantitative analysis method to reconstruct the molecular machinery behind the multiplexed FRET phenomenon. The system measures fluorescence lifetime, intensity and anisotropy as images of excitation-emission matrices (EEM) in real time and high speed within a single image scan, performs high-resolution deep-penetrating 3D FRET imaging in live samples, and fully analyzes all possible photon pathways of multiplexed FRET. The system provides a way for systematic and dynamic imaging of biochemical networks in cells, tissue and live animals, which will help to understand mechanisms of genetic disorders, cancers, and more.

16 Claims, 12 Drawing Sheets

(56) References Cited

OTHER PUBLICATIONS

M. Elangovan, R. N. Day, and A. Periasamy, "Nanosecond fluorescence resonance energy transfer-fluorescence lifetime imaging microscopy to localize the protein interactions in a single living cell," Journal of Microscopy-Oxford 205, 3-14 (2002).

S. C. Blanchard, H. D. Kim, R. L. Gonzalez, J. D. Puglisi, and S. Chu, "tRNA dynamics on the ribosome during translation," Proceedings of the National Academy of Sciences of the United States of America 101, 12893-12898 (2004).

S. Kumar, D. Alibhai, and A. Margineanu, FLIM FRET Technology for Drug Discovery: Automated Multiwell-Plate High-Content Analysis, Multiplexed Readouts and Application in Situ—Kumar—2011—ChemPhysChem—Wiley Online Library, (2011) 609-626.

H. Wallrabe and A. Periasamy, "Imaging protein molecules using FRET and FLIM microscopy," Current Opinion in Biotechnology 16, 19-27 (2005).

W. Becker, A. Bergmann, M. A. Hink, K. Konig, K. Benndorf, and C. Biskup, "Fluorescence lifetime imaging by time-correlated single-photon counting," Microscopy Research and Technique 63, 58-66 (2004).

P.T.C. So, T. French, W.M. Yu, K.M. Berland, C.Y. Dong, and E. Gratton, "Time-resolved fluorescence microscopy using two-photon excitation," Bioimagin 3, 49-63 (1995).

M. J. Cole, J. Siegel, S. E. D. Webb, R. Jones, K. Dowling, P. M. W. French, M. J. Lever, L. O. D. Sucharov, M. A. A. Neil, R. Juskaitis, and T. Wilson, "Whole-field optically sectioned fluorescence lifetime imaging," Optics Letters 25, 1361-1363 (2000).

D. M. Grant, J. McGinty, E. J. McGhee, T. D. Bunney, D. M. Owen, C. B. Talbot, W. Zhang, S. Kumar, I. Munro, P. M. P. Lanigan, G. T. Kennedy, C. Dunsby, A. I. Magee, P. Courtney, M. Katan, M. A. A. Neil, and P. M. W. French, "High speed optically sectioned fluorescence lifetime imaging permits study of live cell signaling events," Optics Express, 15656 (2007).

W. Becker, A. Bergmann, and C. Biskup, "Multispectral fluorescence lifetime imaging by TCSPC," Microscopy Research and Technique 70, 403-409 (2007).

P. de Beule, D. M. Owen, H. B. Manning, C. B. Talbot, J. Requejo-Isidro, C. Dunsby, J. McGinty, R. K. Benninger, D. S. Elson, I. Munro, M. J. Lever, P. Anand, M. A. Neil, and P. M. French, "Rapid Hyperspectral Fluorescence Lifetime imaging," Microscopy Research and Technique 70, 481 (2007).

T. A. Laurence, X. X. Kong, M. Jager, and S. Weiss, "Probing structural heterogeneities and fluctuations of nucleic acids and denatured proteins," Proceedings of the National Academy of Sciences of the United States of America 102, 17348-17353 (2005).

D. M. Owen, E. Auksorius, H. B. Manning, C. B. Talbot, P. A. A. d. Beule, C. Dunsby, M. A. A. Neil, and P. M. W. French, "Excitation-resolved hyperspectral fluorescence lifetime imaging using a UV-extended supercontinuum source," Opt. Lett. 32, 3408 (2007).

M. Zhao and L. Peng, "Multiplexed fluorescence lifetime measurements by frequency-sweeping Fourier spectroscopy," Optics Letters 35, 2910 (2010).

A. Oldenburg, J. Reynolds, and D. Marks, "Fast-Fourier-domain delay line for in vivo optical coherence tomography with a polygonal scanner," Applied Optics 42, 4606 (2003).

J. A. Levitt, D. R. Matthews, S, M. Ameer-beg, and K. Suhling, "Fluorescence lifetime and polarization-resolved imaging in cell biology," Current Opinion in Biotechnology 20, 28-36 (2009).

R.-A. Lorbeer, M. Heidrich, C. Lorbeer, D. F. Ramirez Ojeda, G. Bicker, H. Meyer, and A. Heisterkamp, "Highly efficient 3D fluorescence microscopy with a scanning laser optical tomograph," Optics Express 19, 5419 (2011).

K.-S. Lee and J. P. Rolland, "Bessel beam spectral-domain high-resolution optical coherence tomography with micro-optic axicon providing extended focusing range," Opt. Lett. 33, 1696-1698 (2008).

R. A. Leitgeb, M. Villiger, A. H. Bachmann, L. Steinmann, and T. Lasser, "Extended focus depth for Fourier domain optical coherence microscopy," Optics Letters 31, 2450 (2006).

L. Liu, J. A. Gardecki, S. K. Nadkarni, J. D. Toussaint, Y. Yagi, B. E. Bouma, and G. J. Tearney, "Imaging the subcellular structure of human coronary atherosclerosis using micro-optical coherence tomography," Nature medicine 17, 1010-1014 (2011).

T. A. Planchon, L. Gao, D. E. Milkie, M. W. Davidson, J. A. Galbraith, C. G. Galbraith, and E. Betzig, "Rapid three-dimensional isotropic imaging of living cells using Bessel beam plane illumination," Nature Methods 8, 417-U468 (2011).

M. Zhao, R. Huang, and L. L. Peng, "Quantitative multi-color Fret measurements by Fourier lifetime excitation-emission matrix spectroscopy," Optics Express 20, 26806-26827 (2012).

T. Zimmermann, J. Rietdorf, and R. Pepperkok, "Spectral imaging and its applications in live cell microscopy," FEBS Letters 546, 87-92 (2003).

Y. Garini, I. T. Young, and G. McNamara, "Spectral Imaging: Principles and Applications," Cytometry Part A 69A, 735-747 (2006).

D. Millican, "Fluorescence lifetime selectivity in excitation-emission matrices for qualitative analysis of a two-component system," Analytical Chemistry 61, 580 (1989).

J. R. Lakowicz and A. Baiter, "Analysis of excited-state processes by phase-modulation fluorescence spectroscopy.," Biophysical Chemistry 16, 117-132 (1982).

P. J. Verveer, A. Squire, and P. I. H. Bastiaens, "Global Analysis of Fluorescence Lifetime Imaging Microscopy Data," Biophysical Journal 78(2000).

* cited by examiner

METHOD OF SIMULTANEOUS FREQUENCY-SWEEPING LIFETIME MEASUREMENTS ON MULTIPLE EXCITATION WAVELENGTHS

This invention was made with government support under Grant No. R00 EB008737 awarded by the National Institutes of Health. The government has certain rights in the invention.

BACKGROUND OF THE INVENTION

All cellular processes are regulated by complex biochemical reactions. The first sign of a disease is often subtle biochemical changes in the reaction network. Multiplexed Foster resonant energy transfer (FRET) (H. J. Carlson and R. E. Campbell, "Genetically encoded FRET-based biosensors for multiparameter fluorescence imaging," Current Opinion in Biotechnology 20, 19 (2009)) imaging provides a systematic way to study complex biochemical processes. At present, real-time studying of complex cellular processes is limited by our inability to study the FRET network among multiple fluorescent labels simultaneously in live cells and animals. The difficulty rises from the complex photon pathway network in a multi-label FRET complex. To apply multiplexed FRET image in live imaging, all photon pathways need to be imaged in parallel (M. Zhao, R. Huang, and L. Peng, "Quantitative multi-color FRET measurements by Fourier lifetime excitation-emission matrix spectroscopy," Optics Express (2012)).

First established by Theodor Förster in the 1940s (T. Forster, "Zwischenmolekulare energiewanderung and fluoreszenz," Annalen Der Physik 2, 55-75 (1948)), Förster resonant energy transfer (FRET) is widely used as a fluorescence spectroscopy method to measure distances between fluorophores on the nanometer scale. FRET occurs when an excited donor fluorophore transfers its energy to an adjacent ground-state acceptor fluorophore through dipole coupling. Through the FRET process, the donor emission is quenched and the acceptor emission is enhanced. This process depends strongly on the distance between molecules in the 1-10 nm range, and can therefore be exploited as a "spectroscopic ruler" (L. Stryer, "Fluorescence energy-transfer as a spectroscopic ruler," Annual Review of Biochemistry 47, 819-846 (1978)). With recent advances in fluorescence proteins, organic dyes and instrumentation, FRET has found an ever increasing range of applications in biological studies, ranging from tracking protein-protein interactions in cellular processes (M. Elangovan, R. N. Day, and A. Periasamy, "Nanosecond fluorescence resonance energy transfer-fluorescence lifetime imaging microscopy to localize the protein interactions in a single living cell," Journal of Microscopy-Oxford 205, 3-14 (2002)), probing DNA/RNA regulations and dynamics (S. C. Blanchard, H. D. Kim, R. L. Gonzalez, J. D. Puglisi, and S. Chu, "tRNA dynamics on the ribosome during translation," Proceedings of the National Academy of Sciences of the United States of America 101, 12893-12898 (2004)), to high-throughput drug screening (S. Kumar, D. Alibhai, A. Margineanu, R. Laine, G. Kennedy, J. McGinty, S. Warren, D. Kelly, Y. Alexandrov, I. Munro, C. Talbot, D. W. Stuckey, C. Kimberly, B. Viellerobe, F. Lacombe, E. W. F. Lam, H. Taylor, M. J. Dallman, G. Stamp, E. J. Murray, F. Stuhmeier, A. Sardini, M. Katan, D. S. Elson, M. A. A. Neil, C. Dunsby, and P. M. W. French, "FLIM FRET technology for drug discovery: automated multiwell-plate high-content analysis, multiplexed readouts and application in situ," Chemphyschem 12, 609-626 (2011)). Most FRET biological studies were carried out with two different fluorophores, of which the donor and acceptor can either be fused with a flexible linker (single-chain FRET) or fused to two different molecules respectively (dual chain FRET). Single-chain FRET is used to detect conformation change in the flexible linker. Dual-chain FRET is used to detect interactions between two molecules.

Fluorescent signals from a FRET system can be represented in terms of excitation-emission matrix (EEM) channels, which are characterized by their individual exciters (which fluorophore absorbs the excitation photon) to emitters (which fluorophore emits the fluorescence photon) pathways. For two-color FRET, three possible EEM channels exist: excitation of the donor and its subsequent fluorescence emission (donor EEM channel or donor self excitation-emissions pathway); excitation of the acceptor and its subsequent emission (acceptor EEM channel or acceptor self excitation-emissions pathway); and excitation of the donor, which excites the acceptor via FRET, followed by emission from the acceptor (FRET EEM channel or FRET pathway). For FRET involving more than two colors, more EEM channels exist, as shown in FIG. 1.

FIGS. 1(a) and 1(b) illustrate an excitation emission matrix (EEM) representation of three-color FRET between fluorescein, Cy3 and Cy5. FIG. 1(a) shows photon pathways in a three-color FRET process. Six possible exciter-to-emitter photon pathways are present: three self excitation-emission EEM channels with Fluorescein, Cy3 and Cy5 ($e_{11}$, $e_{22}$ and $e_{33}$ illustrated in FIG. 1(b)), and three FRET EEM channels ($e_{12}$, $e_{13}$ and $e_{23}$ illustrated in FIG. 1(b)). Each of the three non-FRET EEM channels (e11, e22 and e33 illustrated in FIG. 1(b)) defines a self excitation-emission decay photon pathway. The FRET EEM channel $e_{12}$ is a photon pathway in which photons emitted by donor fluorophores in response to the 488 nm radiation and transfer energy to acceptor fluorophores, which then emit photons of wavelengths in the 550 to 600 nm range as shown in FIG. 1(b), thus defining a FRET photon pathway. This pathway is marked $e_{12}$ in FIG. 1(b). The same is true for FRET EEM channels $e_{13}$ and $e_{23}$. Thus each of the three FRET EEM channels (e12, e13 and e23 illustrated in FIGS. 1(a) and 1(b)) defines a donor excitation-acceptor emission decay photon pathway. FIG. 1(b) is an EEM representation of the three-color FRET as a function of both excitation and emission wavelengths. Different photon pathways occupy different regions of the EEM. For each photon pathway, the excitation spectrum follows the exciter, and the emission spectrum follows the emitter.

Note that in FIG. 1(b), each of the graphical plots depict emissions of the same intensity. Thus, as shown in FIG. 1(b), there are overlaps between the donor EEM channels of Fluorescein and Cy3 ($e_{11}$ and $e_{22}$ in FIG. 1(b)) and a FRET EEM channel from donor Fluorescein to an Acceptor ($e_{12}$ in FIG. 1(b)). There is therefore bleed-through between the two donor channels and the FRET EEM channel. While not shown in FIG. 1(b), there may be additional bleed-through between the channels.

To quantify the absolute FRET efficiency, which is the probability of energy transfer from a donor to an acceptor, the current standard practice is to apply fluorescence lifetime imaging (FLIM) (H. Wallrabe and A. Periasamy, "Imaging protein molecules using FRET and FLIM microscopy," Current Opinion in Biotechnology 16, 19-27 (2005)), a time-resolved fluorescence method, on the donor EEM channel, where the quenching effect of a FRET process causes a lifetime decrease according to equation (1) below.

$$\tau_D^{DonorEEM} = (1-\eta)\tau_0 \tag{1}$$

where $\tau_0$ is the donor lifetime without FRET, and $\eta$ is the FRET efficiency.

In other words, the donor fluorophores involved in a FRET process transfer energy to acceptor fluorophores, causing the donor fluorophores to lose energy in this FRET process and to return to the ground state faster than through the donor EEM channel alone.

Such practice is unsuitable for analyzing multi-color FRET, where multiple FRET processes can affect the lifetime of a donor in the same time, and the donor lifetime alone cannot distinguish different processes. Furthermore, current FLIM techniques still have inferior imaging performances in 3D spatial resolution, speed, and multiplexing ability. 3D point scanning FLIM with either time domain (W. Becker, A. Bergmann, M. A. Hink, K. Konig, K. Benndorf, and C. Biskup, "Fluorescence lifetime imaging by time-correlated single-photon counting," Microscopy Research and Technique 63, 58-66 (2004)) or frequency domain (P. T. C. So, T. French, W. M. Yu, K. M. Berland, C. Y. Dong, and E. Gratton, "Time-resolved fluorescence microscopy using two-photon excitation," Bioimaging 3, 49-63 (1995)) methods are too slow for live imaging. Wide-field FLIM has a faster frame rate, but does not have native 3D section ability, and requires special optical sectioning techniques such as structured illumination (M. J. Cole, J. Siegel, S. E. D. Webb, R. Jones, K. Dowling, P. M. W. French, M. J. Lever, L. O. D. Sucharov, M. A. A. Neil, R. Juskaitis, and T. Wilson, "Whole-field optically sectioned fluorescence lifetime imaging," Optics Letters 25, 1361-1363 (2000)) or spinning disc confocal microscopy (D. M. Grant, J. McGinty, E. J. McGhee, T. D. Bunney, D. M. Owen, C. B. Talbot, W. Zhang, S. Kumar, I. Munro, P. M. P. Lanigan, G. T. Kennedy, C. Dunsby, A. I. Magee, P. Courtney, M. Katan, M. A. A. Neil, and P. M. W. French, "High speed optically sectioned fluorescence lifetime imaging permits study of live cell signaling events," Optics Express 15, 15656-15673 (2007)) for 3D imaging, which significantly increases acquisition time and instrumentation complexity. More importantly, existing FLIM techniques are not multiplexing friendly, especially in multi-laser excitation imaging. While emission-multiplexed FLIM can be implemented through multiple detectors (W. Becker, A. Bergmann, and C. Biskup, "Multispectral fluorescence lifetime imaging by TCSPC," Microscopy Research and Technique 70, 403-409 (2007)) or hyperspectral imaging (P. De Beule, D. M. Owen, H. B. Manning, C. B. Talbot, J. Requejo-Isidro, C. Dunsby, J. McGinty, R. K. P. Benninger, D. S. Elson, I. Munro, M. J. Lever, P. Anand, M. A. A. Neil, and P. M. W. French, "Rapid hyperspectral fluorescence lifetime imaging," Microscopy Research and Technique 70, 481-484 (2007)), previous excitation-multiplexed FLIM techniques use a time-sharing scheme on multiple excitation wavelengths (T. A. Laurence, X. X. Kong, M. Jager, and S. Weiss, "Probing structural heterogeneities and fluctuations of nucleic acids and denatured proteins," Proceedings of the National Academy of Sciences of the United States of America 102, 17348-17353 (2005); D. M. Owen, E. Auksorius, H. B. Manning, C. B. Talbot, P. A. A. de Beule, C. Dunsby, M. A. A. Neil, and P. M. W. French, "Excitation-resolved hyperspectral fluorescence lifetime imaging using a UV-extended supercontinuum source," Optics Letters 32, 3408-3410 (2007)), which requires specialized laser sources with sophisticated laser control and further prolongs the already slow FLIM image acquisition.

It is therefore desirable to provide improved systems able to measure time-resolved excitation-emission fluorescence signals from a sample, where the above short comings are alleviated.

SUMMARY OF THE INVENTION

One embodiment of the invention is directed to an apparatus for measuring time-resolved excitation-emission of a sample. The apparatus comprises an interferometer that includes an optical delay line, and a multi-wavelength radiation source providing an input laser beam of radiation of multiple wavelengths to the interferometer. The interferometer provides an excitation radiation beam of said multiple wavelengths for scanning the sample and exciting fluorophores in the sample. The fluorophores emit an emission radiation beam in response to the excitation radiation beam. The optical delay line comprises a rotating polygonal mirrored surface and optics that cause the input beam to impinge onto the polygonal mirrored surface at least four times. The polygonal mirrored surface reflects the input beam to provide the excitation radiation beam. Frequency-sweeping laser modulations from 0 to at least 10 MHz through interference in the excitation radiation beam are generated at an interference modulation frequency that is linear to the path-length scanning speed of the rotating polygonal mirrored surface. The apparatus includes a scanning mechanism to scan the excitation radiation beam across the sample, and a plurality of modulation detectors detecting separately different wavelength components of said excitation radiation beam to provide excitation modulation signals. The apparatus further comprises a plurality of emission detectors detecting separately different wavelength components of the emission radiation beam to acquire an image of the sample to provide emission signals; and an instrument analyzing the excitation modulation signals and the emission signals to determine with at least nanosecond accuracy a time-resolved signal or signals of one or more excitation-emission photon pathways in the sample.

One more embodiment of the invention is directed to an apparatus for measuring a sample, comprising optics that focus a radiation beam to the sample in a scanning-laser optical tomography configuration, the optics comprising a beam shaper that shapes said radiation beam into a Bessel beam that is focused to the sample. The apparatus includes a transmission detector that detects radiation from the radiation beam that is transmitted through the sample; and at least one second detector that detects radiation from the sample along an optical path away from direction of the radiation beam.

Another embodiment of the invention is directed to measuring time-resolved excitation-emission of a sample. An input laser beam of radiation of multiple wavelengths is provided to an interferometer that includes an optical delay line, causing the interferometer to provide an excitation radiation beam of said multiple wavelengths. The optical delay line comprises a rotating polygonal mirrored surface. The sample is scanned and fluorophores in the sample are excited using the excitation radiation beam. The fluorophores emit an emission radiation beam in response to the excitation radiation beam. The input beam is caused to impinge onto the polygonal mirrored surface which reflects the input beam to provide the excitation radiation beam, wherein frequency-sweeping laser modulations from about 0 to at least 10 MHz through interference in the excitation radiation beam are generated at an interference modulation frequency that is linear to the path-length scanning speed of the rotating polygonal mirrored surface. The excitation radiation beam is scanned across the sample. Different wavelength components of the excitation radiation beam are detected separately to provide excitation modulation signals. Different wavelength components of the emission radiation beam are detected to acquire an image of the sample to provide emission signals. The excitation modulation signals and emission signals are analyzed to determine with at least nanosecond resolution a time-resolved signal or signals of one or more excitation-emission photon pathways in the sample. The analysis of the excitation modulation signals and emission signals includes mixing an excitation modulation signal provided in response to a detected wavelength component of the excitation radiation beam and an emission signal provided in response to a detected wavelength component of the emission radiation beam to provide a high frequency component and a low frequency component, attenuating or removing the high frequency component and digitizing the low frequency component.

Yet another embodiment of the invention is directed to an apparatus for measuring time-resolved excitation-emission of a sample, comprising an interferometer that includes an optical delay line and a multi-wavelength radiation source providing an input beam of radiation of multiple wavelengths to the interferometer. The interferometer provides an excitation radiation beam of the multiple wavelengths for scanning the sample and exciting fluorophores in the sample. The fluorophores emit an emission radiation beam in response to the excitation radiation beam. The optical delay line comprises a rotating polygonal mirrored surface and optics that causes the input beam to impinge onto the polygonal mirrored surface which reflects the input beam to provide the excitation radiation beam. Frequency-sweeping laser modulations from 0 to at least 10 MHz through interference in the excitation radiation beam are generated at an interference modulation frequency that is linear to the path-length scanning speed of the rotating polygonal mirrored surface. The apparatus includes a mechanism scanning the excitation radiation beam across the sample, a plurality of modulation detectors detecting separately different wavelength components of the excitation radiation beam to provide excitation modulation signals and a plurality of emission detectors detecting separately different wavelength components of the emission radiation beam to acquire an image of the sample to provide emission signals. The apparatus also comprises an instrument analyzing the excitation modulation signals and emission signals to determine with at least nanosecond resolution a time-resolved signal or signals of one or more excitation-emission photon pathways in the sample. The instrument comprises a plurality of RF mixers, each of the RF mixers mixing an excitation modulation signal provided in response to a detected wavelength component of the excitation radiation beam and an emission signal provided in response to a detected wavelength component of the emission radiation beam to provide a high frequency component and a low frequency component. The instrument further comprises a low pass filter attenuating the high frequency component and an analog to digital converter that digitizes the low frequency component.

Still another embodiment of the invention is directed to an apparatus for measuring Foster resonant energy transfer (FRET) characteristics of a sample with molecules that may be bound or react to an agent, the molecules tagged by donor fluorophores with a donor excitation-donor emission decay photon pathway and one FRET photon pathway. The apparatus comprises a device measuring time-resolved fluorescence signal intensities with at least nanosecond time resolution of donor fluorophores in the sample in the donor self excitation-emission photon pathway and in the FRET photon pathway substantially simultaneously and a processor calculating from the time-resolved fluorescence signal intensities an average decay life time of donor fluorophores in the sample in the donor self excitation-emission photon pathway and an average decay life time of such type of donor fluorophores in the FRET photon pathway; and deriving FRET efficiencies associated with bound/reacted and unbound/unreacted donor fluorophores.

Yet one more embodiment of the invention is directed to an apparatus for measuring Foster resonant energy transfer (FRET) characteristics of a sample with multiple molecular species, the multiple molecular species tagged by fluorophores with multiple self excitation-self emission photon pathways and multiple FRET photon pathways. The apparatus comprises a device measuring time-resolved fluorescence intensities with at least nanosecond resolution of each type of fluorophore in the sample in self excitation-emission decay photon pathways and in all FRET photon pathways substantially simultaneously and a processor calculating from the time-resolved fluorescence intensities of multiple self excitation-emission decay photon pathways and multiple FRET photon pathways FRET efficiencies of multiple FRET processes and fractions of fluorophores that participate in such FRET process. The processor calculates FRET efficiencies of multiple FRET processes by performing sequential fluorescence decay analysis on all excitation-emission channels, starting with the channel with the longest excitation wavelength, and then proceeding to the channels with sequentially shorter excitation wavelengths, such that in each channel, no more than one fluorescence decay time constant is solved.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

BRIEF DESCRIPTION OF THE DRAWINGS

Identical components in this application are labeled by the same numerals.

DETAILED DESCRIPTION OF EXEMPLARY EMBODIMENTS

Figure 1A:
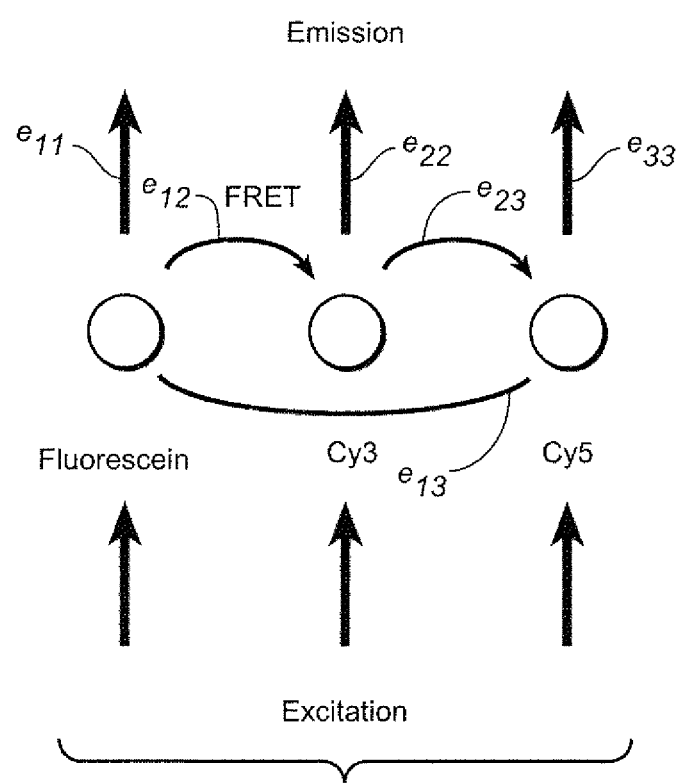
FIGS. 1(a) and 1(b) illustrate an excitation emission matrix (EEM) representation of three-color FRET between fluorescein, cy3 and cy5.

Our invention includes a FLIM microscopic system, titled Fluorescence Excitation-Emission Matrix (FLEEM) imaging system, that can rapidly and simultaneously image time-resolved fluorescence signals in all EEM channels, methods for performing 3D time-resolved EEM imaging with high-resolution in biological samples, and analysis methods for quantifying two-color and multi-color FRET in live samples based on the time-resolved EEM images.

I. Fluorescence Excitation-Emission Matrix (FLEEM) Imaging can Measure Time-Resolved EEM Images Imaging time-resolved EEM at high speed requires simultaneously detecting all possible excitation-emission channels (M. Zhao, R. Huang, and L. Peng, "Quantitative multi-color FRET measurements by Fourier lifetime excitation-emission matrix spectroscopy," Optics Express (2012)). Whereas imaging at multiple emission wavelengths is easy with dispersive or filtering optics and a detector array, imaging with multiple excitation sources at the same time and being able to distinguish contributions of individual excitation sources simultaneously was not possible before our invention. Previous multi-excitation fluorescence instruments use a time-sharing scheme on excitation channels, which prolongs the imaging acquisition as more excitation channels are added. The time-sharing method is slow for 2D imaging of live samples, and impossible for 3D live imaging.

We previously reported a Fourier transform fluorescence lifetime spectrometer that can simultaneously measure fluorescence lifetimes at multiple laser excitation wavelengths (M. Zhao and L. Peng, "Multiplexed fluorescence lifetime measurements by frequency-sweeping Fourier spectroscopy," Optics Letters 35, 2910 (2010)). The spectrometer contains an interferometer with a fast optical delay line, which generates frequency-sweeping laser modulations through interference. Because the interference modulation frequency is linear to the path-length scanning speed and wavenumber, multiple excitation lines are naturally separated by their different modulation frequencies. When fluorophores are excited by the Fourier modulated multiple excitation sources, fluorescence emission associated with different excitation wavelengths can be resolved by the inverse Fourier analysis. By changing the path-length scanning speed, which changes interferometric modulation frequencies, emission responses at different modulation frequencies can be measured. The fluorescence lifetimes at multiple excitation lines can then be extracted with the frequency domain lifetime method (J. R. Lakowicz, "Principles of Fluorescence Spectroscopy, Third Edition," Springer (2006)). The spectrometer demonstrated nanosecond fluorescence lifetime measurements within 45.5 microseconds at multiple excitation wavelengths. In combination with multi-emission detection and laser scanning imaging, the Fourier transform fluorescence lifetime spectroscopic method in principle will image time-resolved EEM at high speed to capture dynamic biological processes.

In this prior design, an optical delay line consists of a rotating polygon mirror scanner (24 facets, 2.5 inch diameter, 54000 RPM, Lincoln Lasers), a lens and a flat mirror [28]. As one of the 24 mirror facets rotates through a small angle $\theta$ from its normal position, the differential path length of the interferometer changes to $\delta D=4R[1-\cos(\theta)]\sim 2R\theta$, where R is the radius of the polygon mirror array. The instantaneous path-scan speed changes linearly from approximately $-94$ m/s to $+94$ m/s in 45.5 µs. At the interferometer's output, laser lines are modulated at a fast frequency sweep from over 100 MHz to 0 then back to over 100 MHz. The frequency-sweeping modulation allows frequency domain lifetime measurements over a continuous frequency span at a maximal rate of 44,000 point/s (23 µs per point) if decreasing and increasing frequency scans are used for separate points. Resulting lifetimes are within ±10% of literature values [23].

However, the previous spectrometer has two drawbacks: 1) The single-pass optical delay causes unintended walk-off on the laser beam, making the system incompatible with imaging, which requires the laser beam position to move precisely on demand; 2) The signal processing method generates data at a gigabytes rate, which is much faster than the data rate a personal computer (PC) can sustain. As the result, the previous system is incompatible with microscopic imaging. Our invention solves these technique challenges making it possible to form time-resolved EEM images of live samples.

The schematic of the FLEEM imaging system is shown below. The system consists of a multi-wavelength laser source, an interferometer that has an optical delay line in one arm, a laser scanning imaging module that scans the excitation laser within a sample, a detector array module that collects the fluorescent emission, a laser modulation monitoring module that measures laser interferemetric modulation in real time, and a signal processing module that processes and stores signals from the emission detectors and the laser modulation detectors.

Figure 2A:
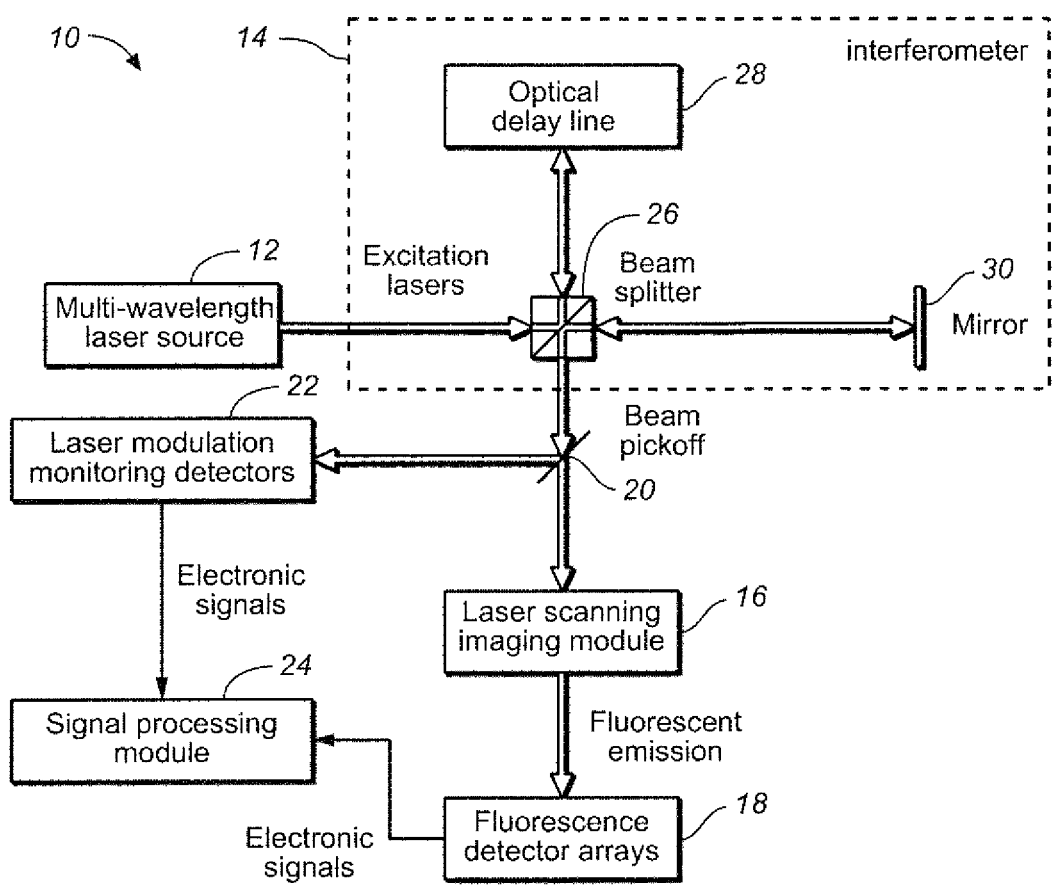
FIG. 2(a) is a block diagram of a FLEEM imaging system to illustrate one embodiment of the invention.

FIG. 2(a) is a block diagram of a FLEEM imaging system 10 to illustrate one embodiment of the invention. As shown in FIG. 2(a), a multi-wavelength laser source 12 supplies an input laser beam of multiple wavelengths to an interferometer 14 which converts the laser beam into an exit beam which is supplied to a laser scanning imaging module 16 to measure a sample in module 16. The different wavelength components of the exit beam cause the fluorophores in the sample to emit radiation, through the self excitation-emission and FRET pathways, of different wavelength components in an emission beam which is detected by fluorescence detector arrays 18, A portion of the exit beam from the interferometer is picked off by a beam-pickoff 20. and supplied to laser modulation monitoring detectors 22. The outputs of detectors 22 and of array 18 are sent to a signal processing unit 24 for determining time-resolved excitation-emission of the sample. Interferometer 14 includes beam splitter 26, which reflects a portion of the input beam towards optical delay line 28, and passes the remainder of the input beam to mirror 30. The reflection of the input beam portion by mirror 30 becomes the reference beam in interferometer 14.

Figure 2B:
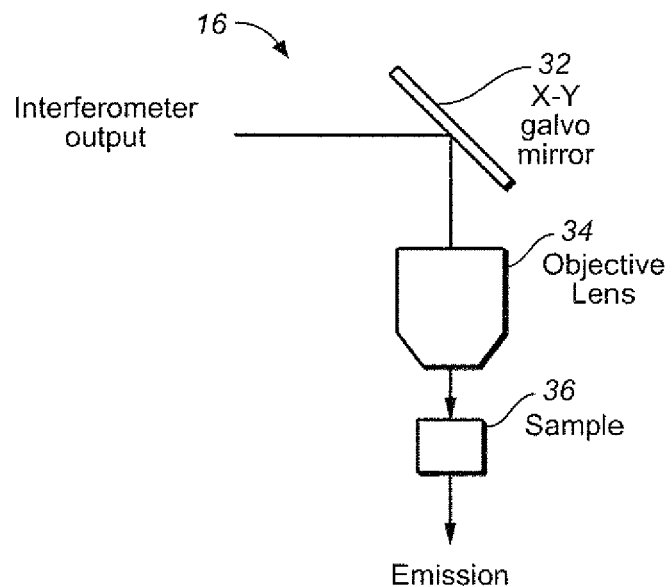
FIG. 2(b) is a schematic diagram of the laser scanning imaging module of FIG. 2(a).

FIG. 2(b) is a black diagram of the laser scanning imaging module 16. The laser output from the interferometer 14 is deflected by an x-y galvo mirror 32, which scans the laser excitation beam across the sample 36 through an objective lens 34. Emission from the sample is detected by fluorescence detector arrays 18 as shown in FIG. 2(a).

Configurations of each module are explained below:

I-1) Optical Delay Line 28: Double-pass optical delay line that allows Fourier excitation nonasecond accuracy lifetime measurements in multiple excitation wavelengths in a raster-scanning imaging mode.

Doubling the Imaging Speed to 88,000 pixel/s

One embodiment of our invention can double the imaging speed of the Fourier, lifetime compared to the prior design described above (e.g. to 88,000 pixel/s). The incident ray is deflected twice by the polygon scanner before being retro-reflected back. If the same 24-facet mirror is used, the frequency sweeping range doubles, and the minimal detectable lifetime becomes 200 picoseconds. However, aberrations in the optical delay line also double, and the frequency range may be cut short by a decreased interference contrast. Thus we prefer to double the facet number to 48 at the same time. As a result the frequency range remains the same but the imaging speed is increased to 88,000 pixel/s. With a 48-facet mirror, the angle range of deflected rays (15°) is half of the current setup (30°). The decreased angle range decreases aberrations, maintains good interference modulations in excitation sources, and improves signal to noise performance of lifetime measurements. This allows lifetime measurements with at least nanosecond resolution. In addition, frequency-sweeping laser modulations from about 0 to at least 10 MHz through interference in the excitation radiation beam are generated at an interference modulation frequency that is linear to the path-length scanning speed of the rotating polygonal mirrored surface.

Figure 3A:
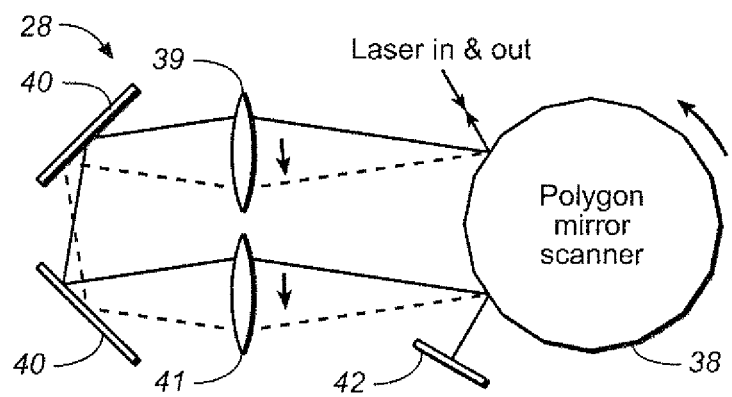
FIGS. 3(a), 3(b) and 3(c) illustrate three possible configurations of the double-passed optical delay line used in the interferometer of FIG. 2(a).
Figure 3B:
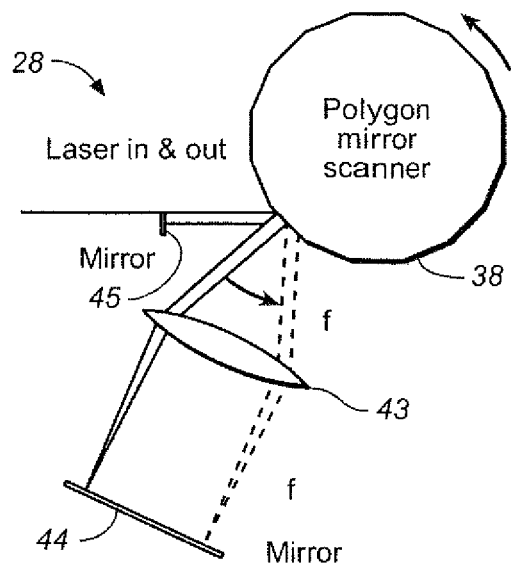
Figure 3C:
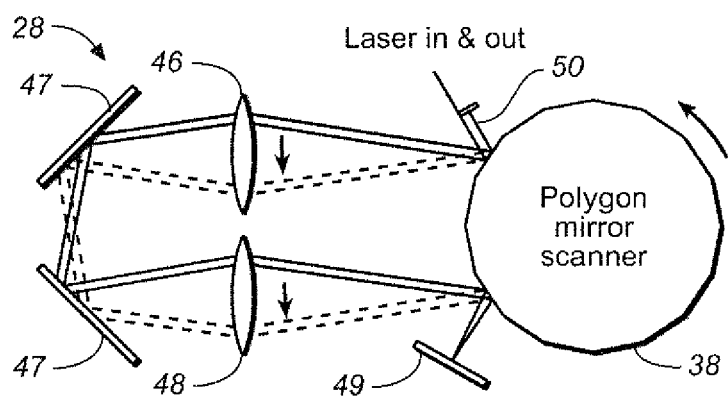

FIGS. 3(a), 3(b) and 3(c) illustrate three possible configurations of the double-passed optical delay line. All configurations eliminate the beam walk-off phenomena in the output laser beam, i.e., unlike the previous single-pass delay line, the laser output from the double-pass delay line is stationary regardless of the movement of the polygon mirror. The stationary laser output makes it possible to scan the excitation laser on demand and forms images in samples.

FIGS. 3(a), 3(b) and 3(c) illustrate three possible configurations of double-pass optical delay line 28 in the interferometer 14 of FIG. 2(a). All three designs enable the laser beam to be reflected off the polygon mirror 38 for 4 or more times. The laser is incident on one facet of the polygon mirror scanner 38 first. The reflected laser is redirected to the polygon mirror 38 for three or more times through a lens or lenses (39 and 41 in FIG. 3(a), or 43 in FIG. 3(b), or 46 and 48 in FIG. 3(c)) and mirrors (40 and 42 in FIG. 3(a), or 44 and 45 in FIG. 3(b), or 47, 49 and 50 in FIG. 3(c)), before exiting out from the delay line 28. The polygon mirror scanner 38 in scanner 28 is rotated by a motor (not shown) at the speed in the range of about 100 to about 5000 revolutions per minute. As the polygon mirror 38 rotates, the laser path changes within the optical delay line (from solid lines to dashed lines), but the location and direction of the exiting laser remains substantially stationary with no walk off. It should be noted that none of the scanners 28 in FIGS. 3(a), 3(b) and 3(c) contains any diffraction elements.

Polygon mirror scanner has been used in the optical delay line of optical coherence tomography previously. However, the design used in optical coherence tomography can only produce laser modulation in the low MHz range, which is not sufficient for fluorescence lifetime measurements. To measure time-resolved fluorescence signal with nanosecond accuracy, the interference modulation will need to be variable between 0 to at least 10 MHz, which was never achieved before our invention.

1-2) Detector Array, Laser Modulation Monitoring Array and Signal Processing Module:

Configurations for measuring lifetime, intensity and anisotropy of multiple excitation-emission channels in parallel The FLEEM imaging system requires two sets of detector arrays, the fluorescent emission detector array and the laser modulation monitoring detector array. Emission signals of different wavelengths, detected by the emission detector array, are mixed with excitation laser modulations, detected by laser modulation monitoring detectors. The resulting demodulated signals are digitized and sent to a PC for further processing.

Figure 4:
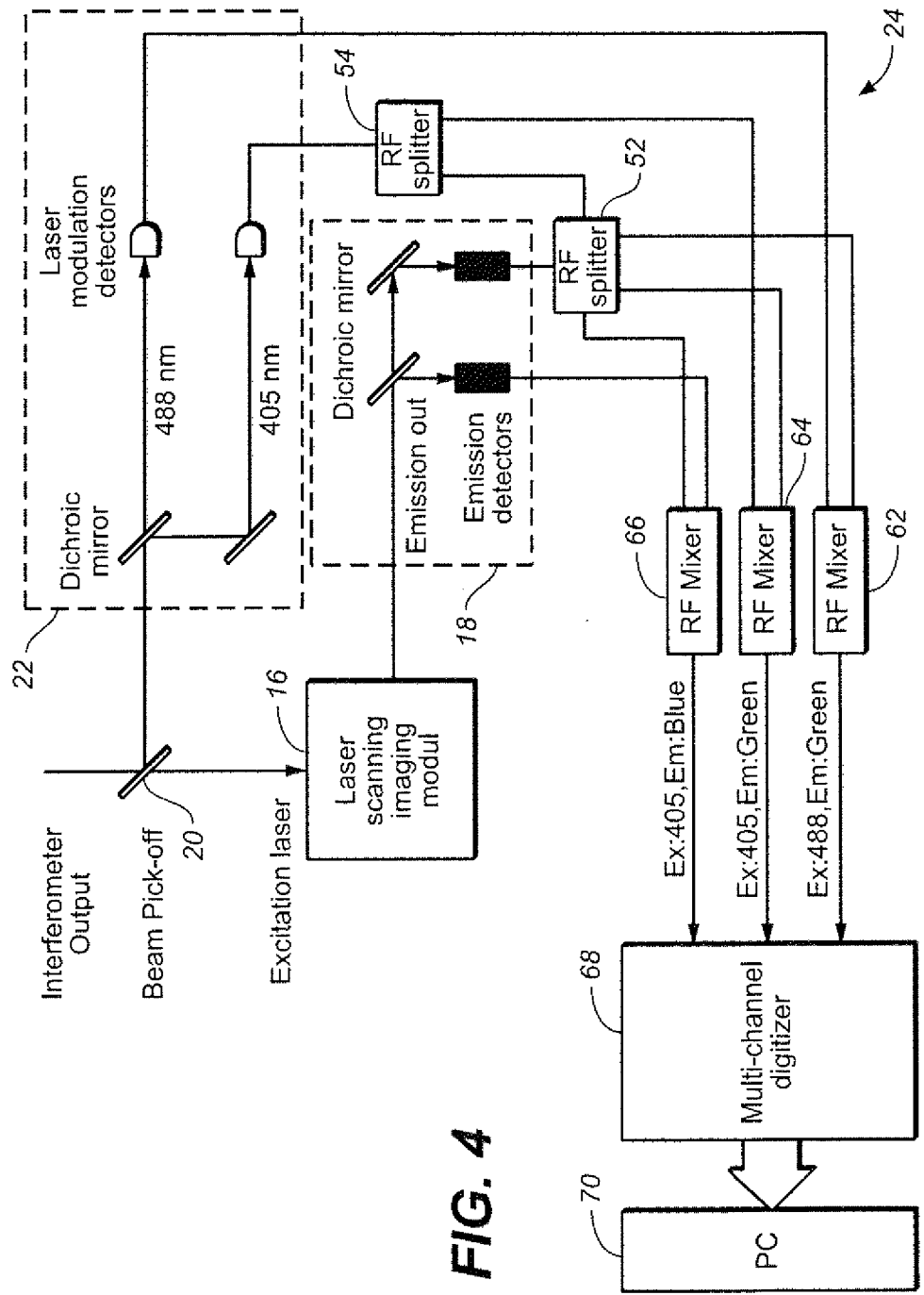
FIG. 4 is a block diagram illustrating a system for imaging lifetime and intensity EEMs of a two-color FRET sample, of which the laser source has two wavelengths (488 nm and 405 nm), and the emission is split by a dichroic mirror into two emission color (blue and green) to illustrate one embodiment of the invention.

FIG. 4 is a block diagram illustrating a system for imaging lifetime and intensity EEMs of a two-color FRET sample, of which the laser source has two wavelengths (488 nm and 405 nm), and the emission is split by a dichroic mirror into two emission colors (blue and green) to illustrate one embodiment of the invention. Three possible EEM channels exist: excitation of the donor by 405 nm photons and donor subsequent fluorescence emission as blue light (donor EEM channel); excitation of the acceptor by 488 nm photons and acceptor subsequent emission as green light (acceptor EEM channel); and excitation of the donor by 405 nm photons, in which donor then emits photons to excite the acceptor via FRET, followed by emission as green light from the acceptor (FRET EEM channel).

As shown in FIG. 4, the laser modulated excitation beam with 488 nm and 405 μm wavelength components is supplied by the interferometer 14 to the laser scanning imaging module 16 containing the sample to be scanned. In response to the 488 nm and 405 nm wavelength components, the sample emits blue and green wavelength components in an emission beam through EEM and FRET channels. After separation by a dichroic mirror, the 488 nm and 405 nm wavelength components of the laser modulated excitation beam are detected separately by laser modulation detectors 22, which output excitation modulation signals of 488 nm and 405 nm in wavelength.

The blue and green wavelength components of the emission beam from the sample in the laser scanning imaging module 16 are separated by dichroic mirrors and separately detected by emission detectors in array 18, which detectors will separately output blue and green emission signals sent to signal processing module 24. Signal processing module 24 includes RF splitters 52, 54, RF mixers 62, 64, 66, multi-channel digitizer 68 and PC 70. RF splitter 52 splits the green emission signal into two green emission signals that are sent to RF mixers 62 and 64. RF splitter 54 splits the 405 nm wavelength laser modulated excitation signals into two signals that are sent to RF mixers 64 and 66. RF mixer 62 also receives the excitation modulation signal of 488 nm in wavelength from one of the detectors 22. RF mixer 66 also receives the excitation modulation signal of 405 nm in wavelength from the other one of the detectors 22.

The detection of donor EEM channel (the donor excitation by 405 nm photons and donor subsequent fluorescence emission as blue light) may not be needed for some applications. In such instance, RF mixer 66 may be omitted. The outputs of RF mixers 62 and 64 may be adequate for multi-channel digitizer 72 and PC 74 to analyze and determine time-resolved excitation-emission of the sample. For some applications, the detection of acceptor EEM channel (excitation of the acceptor by 488 nm photons and acceptor subsequent emission as green light) may not be needed. In such instance, RF mixer 62 may be omitted. The outputs of RF mixers 66 and 64 may be adequate for multi-channel digitizer 72 and PC 74 to analyze and determine time-resolved excitation-emission of the sample.

Figure 5:
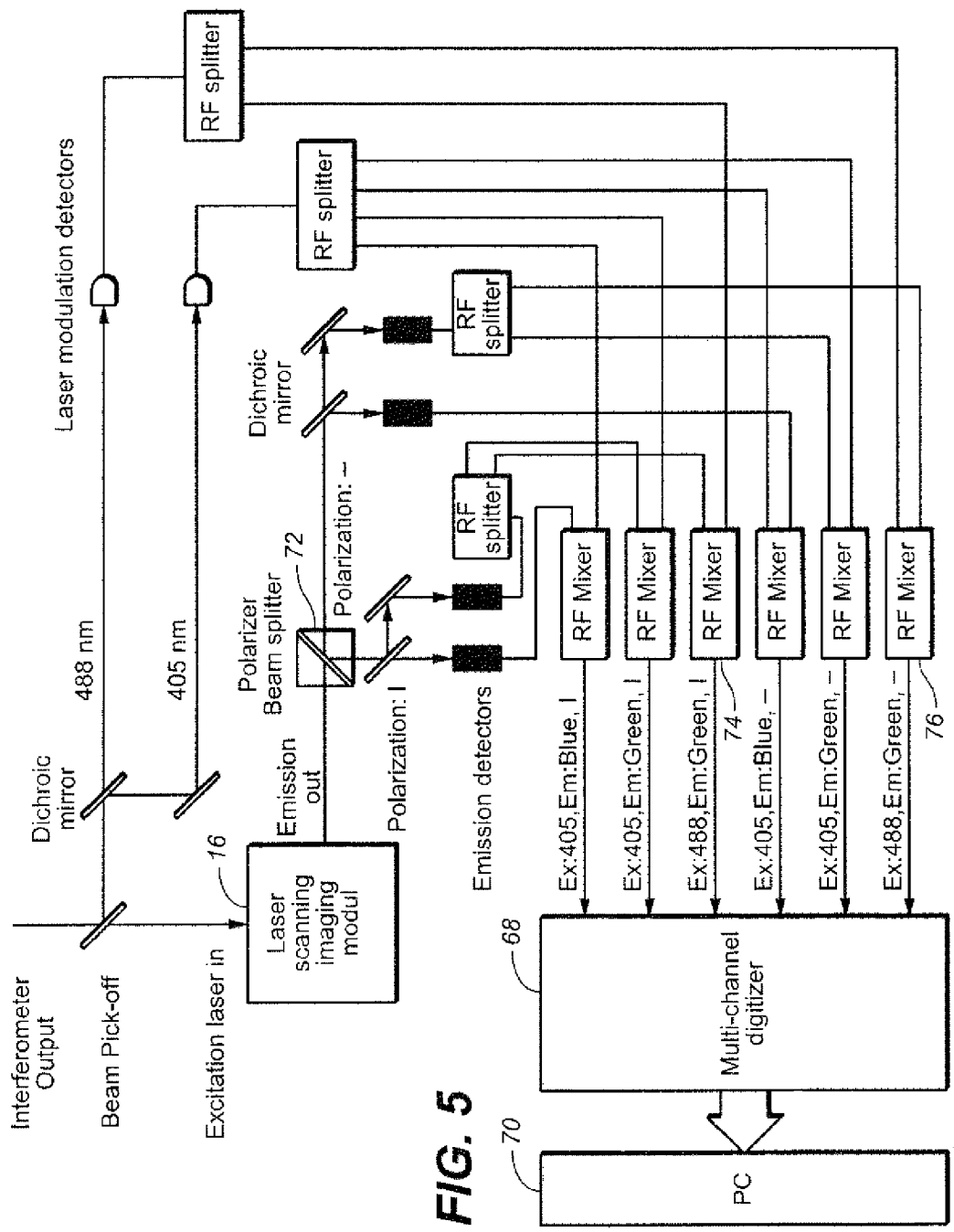
FIG. 5 is a block diagram illustrating a system for imaging lifetime and intensity EEMs of a two-color FRET sample similar to that of FIG. 4 except that the fluorescent emission can be further split into two different polarizations, which produces fluorescent anisotropy, lifetime, and intensity EEM image to illustrate another embodiment of the invention.

Fluorescent emission can be further split into two different polarizations, which produces fluorescent anisotropy, lifetime, and intensity EEM images, as shown in FIG. 5. Time-resolved anisotropy is a quantitative indicator of homo-FRET (FRET within the same fluorescent species) (J. A. Levitt, D. R. Matthews, S. M. Ameer-beg, and K. Suhling, "Fluorescence lifetime and polarization-resolved imaging in cell biology," Current Opinion in Biotechnology 20, 28-36 (2009)), which is used to study intra-species protein interactions in biological sample.

FIG. 5 is a block diagram illustrating a system for imaging lifetime and intensity EEMs of a two-color FRET sample similar to that of FIG. 4 except that the fluorescent emission can be further split into two different polarizations, which produces fluorescent anisotropy, lifetime, and intensity EEM images to illustrate another embodiment of the invention. Thus the emission signals from module 16 include blue and green wavelength components of two different polarizations each. A polarizing beam splitter 72 splits the beam with both blue and green wavelength components by their polarizations and dichroic mirrors then separate the blue and green wavelength components before the four wavelength components are separately detected by four emission detectors. Instead of three RF mixers in FIG. 4, three pairs of RF mixers are used in FIG. 5, each pair mixing the same excitation signal and a pair of emission signals of the same wavelength but different polarizations. Thus, RF mixers 74 and 76 mix the same excitation modulation signal provided from the 488 nm photons and two emission signals provided from green wavelength components of different polarizations. As in the embodiment of FIG. 4, for some applications, detection of the donor EEM channel or of the acceptor EEM channel may not be needed, so that only two pairs of RF mixers may suffice.

The example EEM imaging configuration contains three channels in FIGS. 4 and 5. The number of laser wavelengths, emission colors and the total EEM channels can be increased if more than two colors are used in an imaging study.

In our previous publication (M. Zhao, R. Huang, and L. Peng, "Quantitative multi-color FRET measurements by Fourier lifetime excitation-emission matrix spectroscopy," Optics Express (2012)), laser excitation modulation signals and emission signals were directly digitized at near GHz rate, and the signal processing was performed on the stored raw signal in a PC. The approach generated data at a rate that is much higher than the data transfer/storage rate of a PC software, thus preventing continuous data acquisition, i.e. imaging. In order to decrease the data rate, a common practice in frequency domain lifetime spectroscopy is to mix the emission signal with a reference signal, whose frequency is synchronized but intentionally shifted by a small amount relative to the emission signal frequency. The process demodulates the emission signal to a lower but non-zero frequency signal, which can be acquired at a low digitization rate, transferred to and stored in a regular PC. In conventional frequency domain lifetime spectroscopy, since the emission signal was generated through imposing a fixed frequency modulation on the excitation source, the reference signal can be easily generated by a second signal generator locked to the main signal generator that drives the excitation source (R. Lakowicz, "Principles of Fluorescence Spectroscopy, Third Edition," Springer (2006)).

Figure 6:
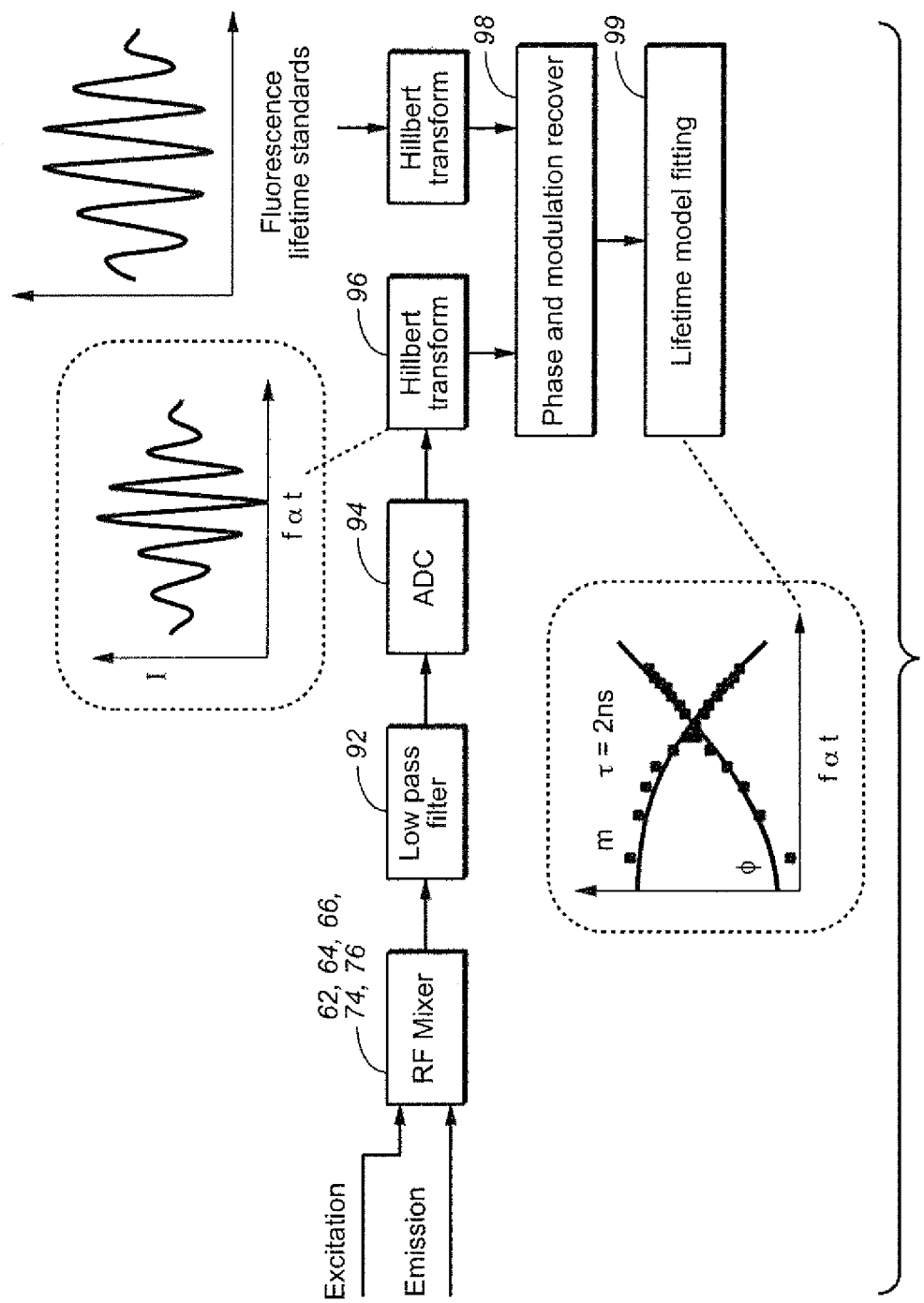
FIG. 6 is a block diagram illustrating an analog-digital-hybrid signal processing system for processing the excitation and emission signals in each EEM channel to illustrate one embodiment of the invention.

In FLEEM, the emission signal's frequency comes from mechanical movements in the delay line rather than an ideal signal source, and is linearly sweeping at an un-lockable speed. Thus a new method for demodulating the emission signal is required. FIG. 6 is a block diagram illustrating an analog-digital-hybrid signal processing system for processing the excitation and emission signals in each EEM channel to illustrate one embodiment of the invention. The corresponding laser excitation and fluorescence emission signals are mixed in an RF mixer (such as one of mixers 62, 64, 66, 74, 76) followed by a low-pass filter 92, and the demodulated emission signal is digitized by analog-to-digital converter 94 at MHz rate, instead of GHz rate as in the previously reported work. In our demodulating method, the reference signal comes from the laser modulation-monitoring detector, which is always at the same frequency as the emission signal. A timing offset is then intentionally applied on the laser modulation signal before it reaches the RF mixer. Because the signal's frequency is linearly changing in time, a small timing offset causes a constant frequency offset on the laser modulation signal, and thus makes it the desired frequency-shifted reference signal. The timing offset is a combination of optical and RF delay. Thus, one may adjust an optical path length difference between the laser modulation wavelength components and the emission wavelength components, or may adjust the relative time delay between the laser modulation signal and the emission signal, or both. The relative time delay between the laser modulation signal and the emission signal can be easily adjusted by changing the length of the RF signal transmission cable.

The digitized signal of an EEM channel is Hilbert transformed (96) and compared (98) with a pre-recorded fluorescence lifetime standard signal to correct for the system RF response. The correct signal is analyzed with the appropriate lifetime model (99). Adjusting the timing offset between the laser modulation signal and the emission signal before reaching the RF mixer allows the processing steps 96, 98 and 99 to be performed at a frequency range of about 100 KHz to about 10 MHz, which is orders of magnitude lower than the operating frequency in the GHz range encountered in a prior design.

II. FLEEM can be Implemented in Multiple Laser-Scanning Imaging Configurations

II-1) Confocal FLEEM

Figure 7:
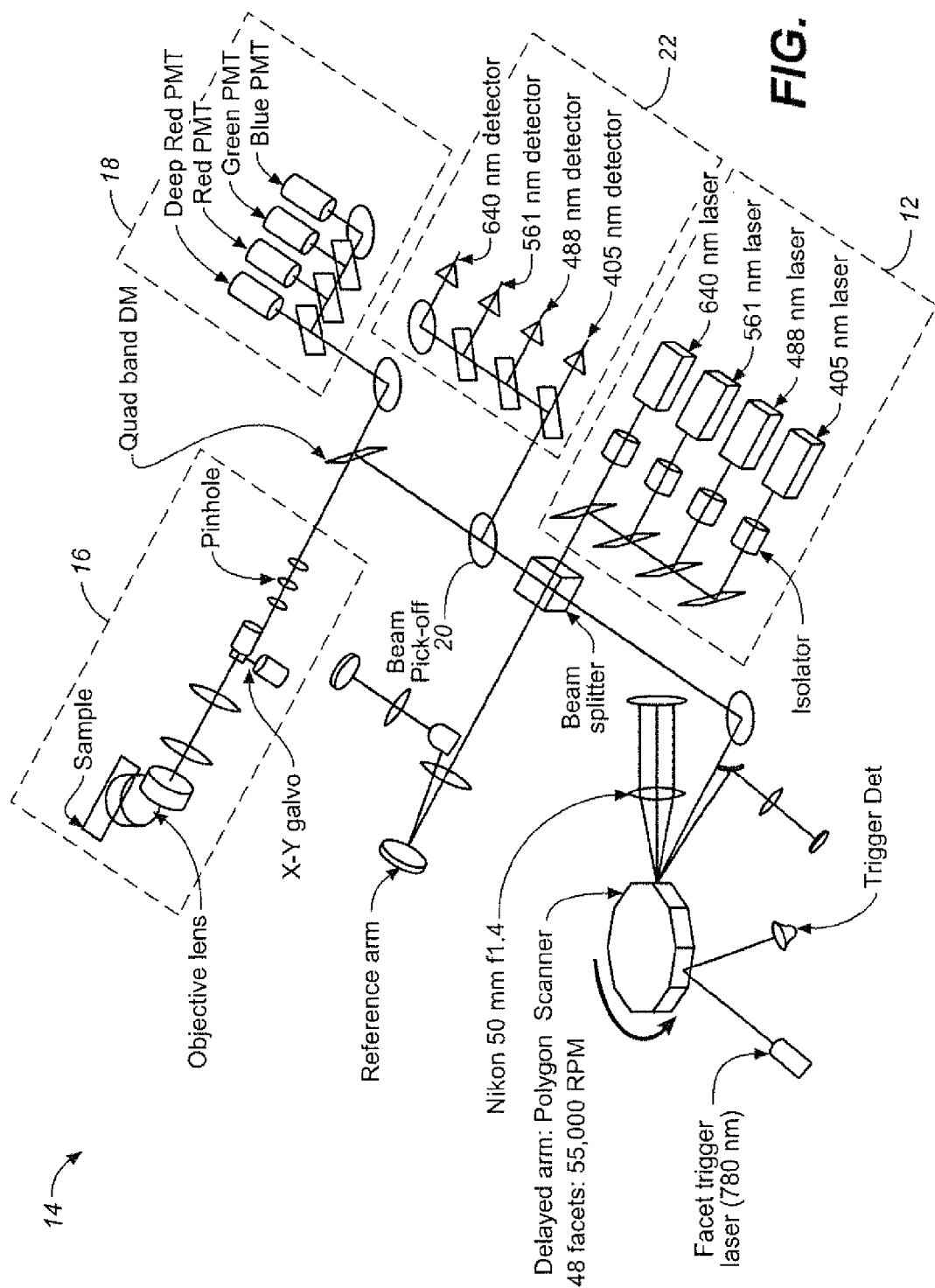
FIG. 7 is a schematic view of a confocal FLEEM microscope, where the laser-scanning imaging module is configured in the confocal scanning mode.

The laser-scanning imaging module can be configured in the confocal scanning mode, with confocal optics that focuses an excitation beam to the sample, as shown as an example configuration in FIG. 7. The confocal FLEEM configuration can provide high-resolution 3D EEM images of live cells and thin tissues.

FIG. 7 is a schematic view of a confocal FLEEM microscope, where the laser-scanning imaging module is configured in the confocal scanning mode. The example configuration has four laser excitation wavelengths and four emission detectors. It is capable of imaging lifetime and intensity in 4-by-4 EEM channels. The optical delay line utilizes the configuration in FIG. 3b.

II-2) SLOT-FLEEM

Alternatively, a scanning-laser optical tomography (SLOT) configuration can be used for imaging thick tissue and live animals, whose thickness is beyond the penetrating depth of confocal imaging. An example configuration is shown in FIG. 8, where optics focuses an excitation beam to the sample.

Figure 8:
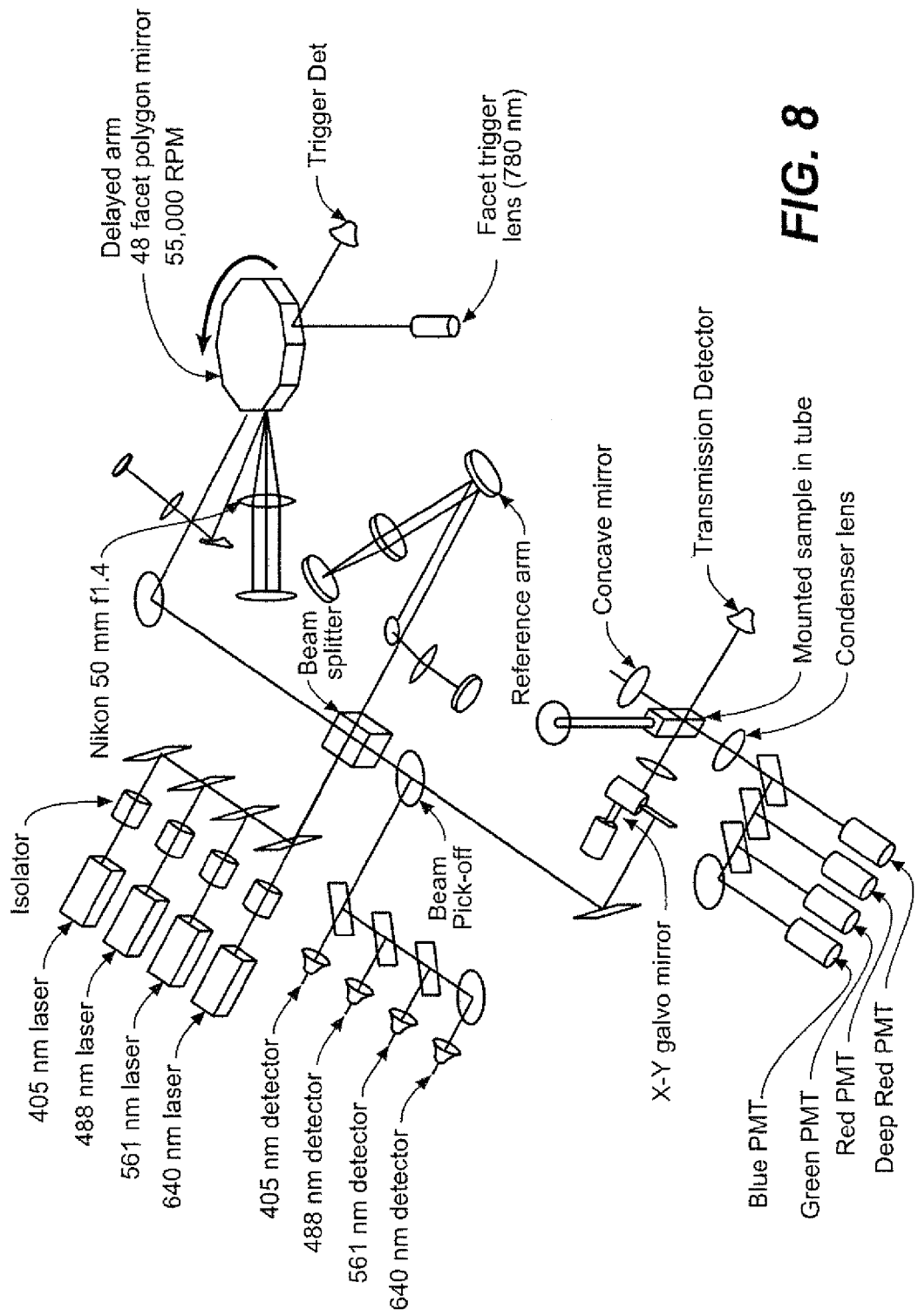
FIG. 8 is a schematic view of a SLOT-FLEEM microscope using a scanning-laser optical tomography (SLOT) configuration for imaging thick tissue and live animals, whose thickness is beyond the penetrating depth of confocal imaging.

FIG. 8 is a schematic view of a SLOT-FLEEM microscope, using a scanning-laser optical tomography (SLOT) configuration for imaging thick tissue and live animals, whose thickness is beyond the penetrating depth of confocal imaging. The example configuration has four laser excitation wavelengths and four emission detectors. It is capable of imaging lifetime and intensity in 4-by-4 EEM channels. The optical delay line utilizes the configuration in FIG. 3b. The sample is placed in a tube and rotated to produce multiple angle projections.

SLOT (R.-A. Lorbeer, M. Heidrich, C. Lorbeer, D. F. Ramirez Ojeda, G. Bicker, H. Meyer, and A. Heisterkamp, "Highly efficient 3D fluorescence microscopy with a scanning laser optical tomograph," Optics Express 19, 5419 (2011)) forms fluorescent projection imaging by scanning a long focused excitation beam through the sample. The total emission signal along the excitation beam path is collected at a 90° angle. The final tomography image is reconstructed from multiple angle projections in the same way as Computer tomography (CT). The penetration depth of SLOT is much larger than confocal imaging, and 3D imaging of live animals such as zebrafish embryos has been successful in our lab.

II-3) Method for High-Resolution SLOT Imaging in Deep Tissue

However, the spatial resolution of SLOT is significantly lower than confocal imaging (10~20 microns vs. less than 1 micron). The resolution of SLOT is solely determined by the excitation beam width within the sample volume. To achieve a large penetration depth, the excitation beam cannot be tightly focused, which would cause the beam to quickly diverge within the sample volume.

Figure 9:
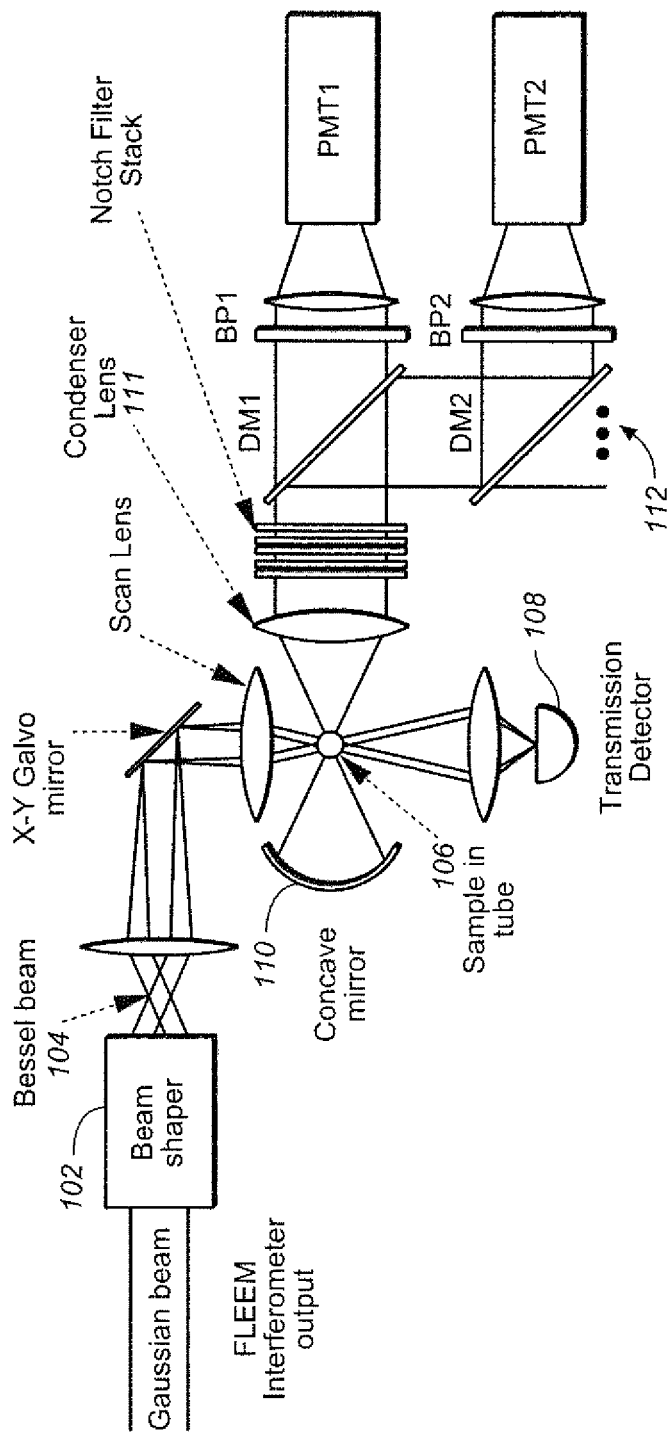
FIG. 9 shows a schematic view of a high-resolution SLOT microscope employing a beam shaper, which converts a regular laser beam to a Bessel beam, in combination with an optional FLEEM input.

Bessel beam illumination has been previously used in Optical Coherence Tomography (K.-S. Lee and J. P. Rolland, "Bessel beam spectral-domain high-resolution optical coherence tomography with micro-optic axicon providing extended focusing range," Opt. Lett. 33, 1696-1698 (2008); R. A. Leitgeb, M. Villiger, A. H. Bachmann, L. Steinmann, and T. Lasser, "Extended focus depth for Fourier domain optical coherence microscopy," Optics Letters 31, 2450 (2006); L. Liu, J. A. Gardecki, S. K. Nadkarni, J. D. Toussaint, Y. Yagi, B. E. Bouma, and G. J. Tearney, "Imaging the subcellular structure of human coronary atherosclerosis using micro-optical coherence tomography," Nature medicine 17, 1010-1014 (2011)) as well as in Bessel beam plane illumination (T. A. Planchon, L. Gao, D. E. Milkie, M. W. Davidson, J. A. Galbraith, C. G. Galbraith, and E. Betzig, "Rapid three-dimensional isotropic imaging of living cells using Bessel beam plane illumination," Nature Methods 8, 417-U468 (2011)) to achieve high-resolution 3D images over extended depth. Using Bessel beam illumination in SLOT enables isotropic high-resolution 3D imaging in large depths. FIG. 9 shows the optical configuration for high-resolution SLOT, in combination with FLEEM. The system allows multiplexed FRET imaging in live animals at a resolution of few microns or better.

FIG. 9 is a schematic view of a High-resolution SLOT microscope employing a beam shaper, which converts a regular laser beam to a Bessel beam, in combination with an optional FLEEM input. The beam shaper 102, which could be an axicon lens, spatial light modulator (SLM) or an optical phase mask, converts a regular laser beam to a Bessel beam 104. The Bessel beam 104 is scanned by means of an X-Y galvo mirror that is rotated by a motor (not shown) across a sample in a tube 106. A portion of the Bessel beam 104 is detected by transmission detector 108. Emission from the sample is collected by mirror 110 and condenser lens 111, and detected by PMT1 and PMT2 after being separated by wavelengths by dichroic mirrors 112.

The high-resolution SLOT can also operate without FLEEM. In such case, only intensity images are acquired, and multiple laser wavelengths, if used, have to be operated in a time-sharing mode.

III. Quantitative FRET Analysis Based on FLEEM Image Data

Time-resolved EEM images produced by the FLEEM imaging system provide a complete characterization of the sample's fluorescence properties. The purpose of a biological imaging study, however, is to detect and quantify the biological characteristics of the sample. Analysis methods of FLEEM aim to connect fluorescence characteristics of a sample undergoing FRET with its biological characteristics, and by doing so to quantitatively measure the biochemical status of the sample.

Currently, lifetime-based FRET imaging studies are limited by not only technical limitations of available lifetime imaging techniques, as discussed earlier, but also data analysis difficulties. FLEEM, a novel lifetime imaging technique, can measure the time-resolved fluorescence responses of FRET on all combinations of excitation and emission wavelengths in the form of an excitation-emission matrix (EEM). The time-resolved EEM represents all exciter-to-emitter photon-pathways that are present in a FRET sample, with each photon-pathway presenting the photophysical properties of the sample in a different angle. By using additional information from the FRET photon-pathway, not available through conventional lifetime imaging methods, minimal computation is required for the FRET analysis. Analyzing FRET with the complete time-resolved EEM, measured by the FLEEM imaging system, allows simple and robust FRET quantification that can analyze complex FRET mixtures without the need to fit multiple unknown decay constants simultaneously (M. Zhao, R. Huang, and L. L. Peng, "Quantitative multi-color FRET measurements by Fourier lifetime excitation-emission matrix spectroscopy," Optics Express 20, 26806-26827 (2012)).

III-1) Bleed-through Correction of Time-Resolved EEM

In an ideal EEM, different exciter-to-emitter photon pathways are completely separated into different EEM channels. However as clearly shown in FIG. 1(b), excitation and emission spectral overlapping between different fluorophores causes spectral bleed-through between different EEM channels (T. Zimmermann, J. Rietdorf, and R. Pepperkok, "Spectral imaging and its applications in live cell microscopy," FEBS Letters 546, 87-92 (2003); Y. Garini, I. T. Young, and G. McNamara, "Spectral Imaging: Principles and Applications," Cytometry Part A 69A, 735-747 (2006)). For instance, the FRET channel between fluorescein and Cy3 (excitation ~488 nm, emission ~580 nm) has three components: signals generated by fluorescein-Cy3 FRET, excitation bleed-through of Cy3, and emission bleed-through of fluorescein. Spectral bleed-through correction is therefore needed in order to recover the ideal EEM.

Spectral bleed-through correction is a key component for all multi-color FRET studies, and has been discussed in detail in both cell imaging and single molecule detection. The majority of these studies present correction methods as a series of linear equations, which can be unified as a single matrix equation in the form of EEM spectral bleed-through correction.

Under the framework of EEM, the relationship between an ideal EEM I and the experimentally measured EEM I' can be written as (D. Millican, "Fluorescence lifetime selectivity in excitation-emission matrices for qualitative analysis of a two-component system," Analytical Chemistry 61, 580 (1989)):

$$I' = B^{Em} I B^{Ex}, \quad (2)$$

where $B^{Em}$ is the emission bleed-through matrix, and $B^{Ex}$ is the excitation bleed-through matrix. The measured EEM I' is an m-by-n matrix, where m is the number of emission spectral channels, and n is the number of excitation spectral channels in the measurement. For a three-color FRET process, I is a 3-by-3 matrix. The emission bleed-through matrix is an m-by-3 matrix and the excitation bleed-through matrix is a 3-by-n matrix. The bleed-through correction procedure aims to recover I from I' with pre-calibrated $B^{Em}$ and $B^{Ex}$ (D. Millican, "Fluorescence lifetime selectivity in excitation-emission matrices for qualitative analysis of a two-component system," Analytical Chemistry 61, 580 (1989)):

$$I=(B^{Em})^{-1}I'(B^{Ex})^{-1} \quad (3)$$

The spectral bleed-through correction is a linear process. Therefore all linear quantities in the EEM form can be corrected as in Equation (3). These include but are not limited to fluorescence intensity, and time-resolved fluorescence decay measurements in the time domain and in the frequency domain.

III-2) an Algorithm for Fast Two-Color FRET Analysis with Minimal Computation

Two-color FRET studies in live cells always probe a mixture of molecules undergoing low/zero FRET and high FRET in chemical equilibrium. While conventional lifetime imaging techniques measure the donor fluorescence decay response only, which is an ensemble average of all donor molecules in each pixel, FRET analysis needs to differentiate two different donor lifetimes based on a single-channel time-resolved measurement. Multi-exponential decay analysis of donor fluorescence decay is thus a mandate for accurate FRET quantification. Multi-exponential fluorescence decay analysis requires high quantity data that are often un-retainable from genetically encoded fluorescent labels in live cells. Global analysis of multi-exponential fluorescence decay is often required for more robust analysis (P. J. Verveer, A. Squire, and P. I. H. Bastiaens, "Global Analysis of Fluorescence Lifetime Imaging Microscopy Data," Biophysical Journal 78(2000)). Global FLIM analysis of large image sets is prohibitively demanding in computing power.

In the format of EEM, a two-color FRET sample has three distinct exciter-to-emitter photon-pathways: donor self excitation-emission (donor EEM channel), acceptor self excitation-emission (acceptor EEM channel), and donor excitation-acceptor emission (FRET EEM channel). After spectral bleed-through correction, the donor and acceptor EEM channels follow the exponential decay model, whereas the FRET channel follows the excited-state reaction model. Conventional FLIM-FRET methods only examine the fluorescence responses from the donor excitation-emission photon-pathway, while FLEEM measures the time-resolved fluorescence response from all three photon-pathways simultaneously.

The donor of a two-color FRET changes its FRET efficiency upon binding or reacting with its target A, $$D^- + A \rightleftharpoons D^+ A, \quad (4)$$

Each donor molecule has one of two possible FRET efficiencies, $\eta^+$ and $\eta^-$, associated with the bound/reacted ($D^+$) and unbound/unreacted ($D^-$) donors, respectively. Each donor molecule may react with or be bound to the target A. The FRET efficiency change could be caused by either the association of a dual-chain sensor, in which case $\eta^-$ is zero, or conformation change of a single-chain FRET sensor, in which case both $\eta^+$ and $\eta^-$ are non-zero.

Time-resolved signals of both the donor EEM channel and the FRET EEM channel are affected by these two FRET efficiencies. By single exponential decay fitting of the donor EEM channel, the average donor lifetime can be obtained as $$\bar{\tau}_D^{Donor} = \frac{(1-\eta^-)^2 + k[A](1-\eta^+)^2}{(1-\eta^-) + k[A](1-\eta^+)} \tau_0, \quad (5)$$

where k is the association constant of the reaction, [A] is the concentration of the binding target, and $\tau_0$ is the lifetime of the free donor.

The FRET EEM channel time-resolved response follows the excited-state reaction mode (J. R. Lakowicz and A. Balter, "Analysis of excited-state processes by phase-modulation fluorescence spectroscopy," Biophysical Chemistry 16, 117-132 (1982)), which, in the frequency domain, is approximately $$\tilde{I}_{FRET}(\omega) \approx \frac{1}{\sqrt{1+\omega^2(\tau_D^{FRET})^2}} \exp[i\tan^{-1}(\omega\tau_D^{FRET})] \times \tilde{I}_A(\omega) \quad (6)$$

where $\tilde{I}_A(\omega)$ is the frequency response of the acceptor, and $\bar{\tau}_D^{FRET}$ is the average lifetime of donor recovered from the FRET EEM channel, given by $$\bar{\tau}_D^{FRET} = \frac{(1-\eta^-)\eta^- + k_a[A](1-\eta^+)\eta^+}{\eta^- + k_a[A]\eta^+} \tau_0. \quad (7)$$

Eq. 5 and Eq. 7 take different forms, although both are weighted averages of bound and unbound donor lifetimes. In the donor EEM channel, the donor lifetime is measured as the average of two donor lifetime components weighed by their spontaneous emission intensities. In the FRET EEM channel, the weighting factor is the FRET transfer intensity of individual donor species. The average donor lifetime recovered from the donor EEM channel is mostly influenced by the donor species with high spontaneous emission (less quenched and with low FRET efficiency), whereas the average donor lifetime recovered from the FRET EEM channel is mostly influenced by the donor species with high FRET intensity (more quenched and with high FRET efficiency).

The combination of Eq. 5 and 7 defines a parametric model describing the relationship between two average donor lifetimes recovered from the donor EEM channel and the FRET EEM channel respectively. Both lifetimes are functions of FRET efficiencies of the bound and unbound donor states $\eta^+$ and $\eta^-$, as well as the concentration of the binding target [A]. As [A] naturally varies from cell to cell, parametric model fitting of multi-cell imaging results will yield the FRET efficiencies $\eta^+$ and $\eta^-$.

The implementation of the above FRET image analysis model requires much less computing time than global double-exponential decay analysis. However, it does require imaging the time-resolved signal of all three EEM channels of two-color FRET, which was not possible before the FLEEM imaging system.

The procedure consists of three steps:

1) The first step starts from cell-averaged time-resolved EEM data produced by FLEEM, which are subjected to EEM bleed-through correction, followed by single exponential decay fitting to extract average donor lifetimes in the donor and FRET EEM channels.

2) The second step applies the simple parametric linear model fitting of Eq. 5 and 7, through which FRET efficiencies of the two donor species can be determined. Once FRET efficiencies of the two donor species are known, in the final step of the analysis procedure, lifetime images of the donor EEM channel can be linearly converted to concentration maps of target molecule A following Eq. 5.

3) The entire process produces robust and highly quantitative FRET image results without double exponential lifetime fitting or global analysis, and can be easily applied to large image sets. We have applied the analysis to live cell imaging of calcium levels, which generates calcium concentration images without the need for intense computing.

III-3) Quantitative Multi-Color FRET Analysis Based on Time-Resolved EEM Measurements Time-resolved EEM measurement results from the FLEEM imaging system can be utilized in investigation of multi-color FRET processes involving three or more fluorophore molecules. Quantification of multi-color FRET could greatly facilitate the understanding of complex cellular processes, which almost always involve multiple components through networks of dynamic interactions. In recent years, several techniques have been developed to enable two-pair or three-color FRET in both in vitro studies and in vivo imaging in live cells (H. J. Carlson and R. E. Campbell, "Genetically encoded FRET-based biosensors for multiparameter fluorescence imaging," Current Opinion in Biotechnology 20, 19 (2009)). These methods are either ratiometric-based or at most partially lifetime-based, which do not provide absolute quantifications.

The key challenge in quantifying multi-color FRET is the significantly increased complexity due to possible multi-way exciter-to-emitter photon-pathways. These pathways have different combinations of excitation and emission wavelengths, and are naturally separated in an EEM into different spectral channels. By analyzing each individual EEM spectral channel, the complex multi-way interactions in a multi-color FRET process can be precisely quantified.

Figure 10:
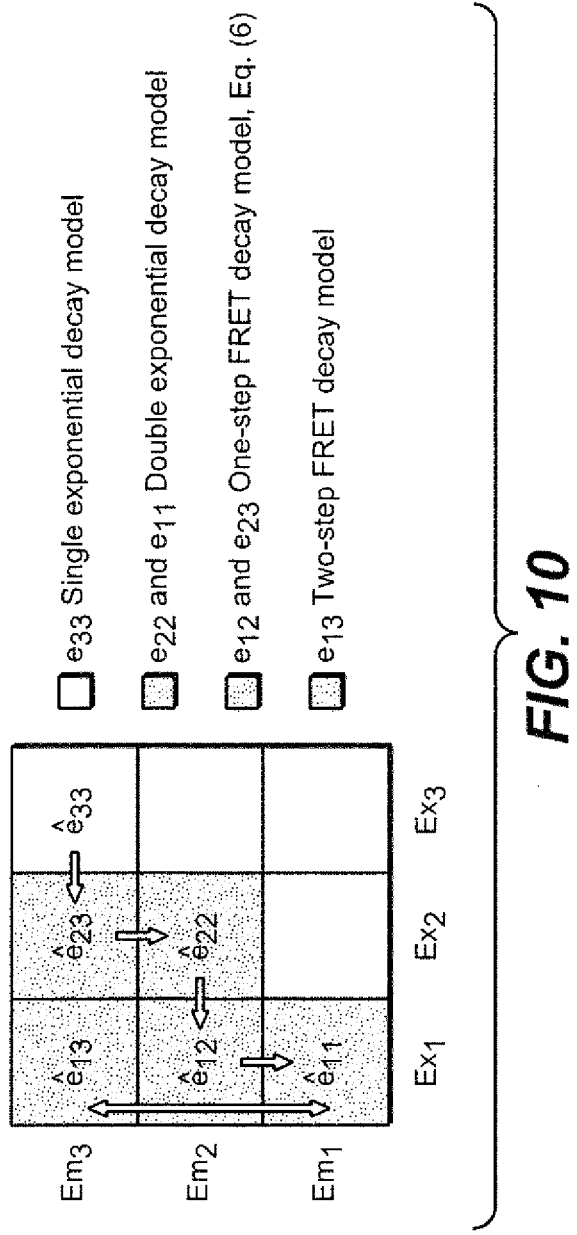
FIG. 10 shows the time-resolved EEM analysis sequence of multi-color FRET.

FIG. 10 shows the time-resolved EEM analysis sequence of multi-color FRET. The analysis is performed on a channel-by-channel basis, with each channel involving only at most one unknown lifetime parameter. EEM channels of three-color FRET (FIG. 1b) in the illustration are coded by their decay models. The analysis first obtains the longest wavelength acceptor (fluorophore No. 3 in case of three-color FRET, for example Cy5 in FIG. 1b) lifetime $\tau_3$ in $\hat{e}_{33}$, then finds quenched lifetime $\tau_2^{123}$ of fluorophore No. 2 (Cy3) in FRET channel $\hat{e}_{23}$. The percentage of quenched fluorophore No. 2 (Cy3), $P_2$ is then calculated from fluorophore 2 EEM channel $\hat{e}_{22}$. The FRET channel $\hat{e}_{12}$ is next, which yields the quenched lifetime $\tau_1^{123}$ of fluorophore No. 1 (fluorescein). The percentage of quenched fluorophore No. 1 (fluorescein), $P_1$ is extracted from the EEM channel $\hat{e}_{11}$, and finally the FRET channel $\hat{e}_{13}$ serves as a verification of the time-resolved EEM analysis.

Figure 1B:
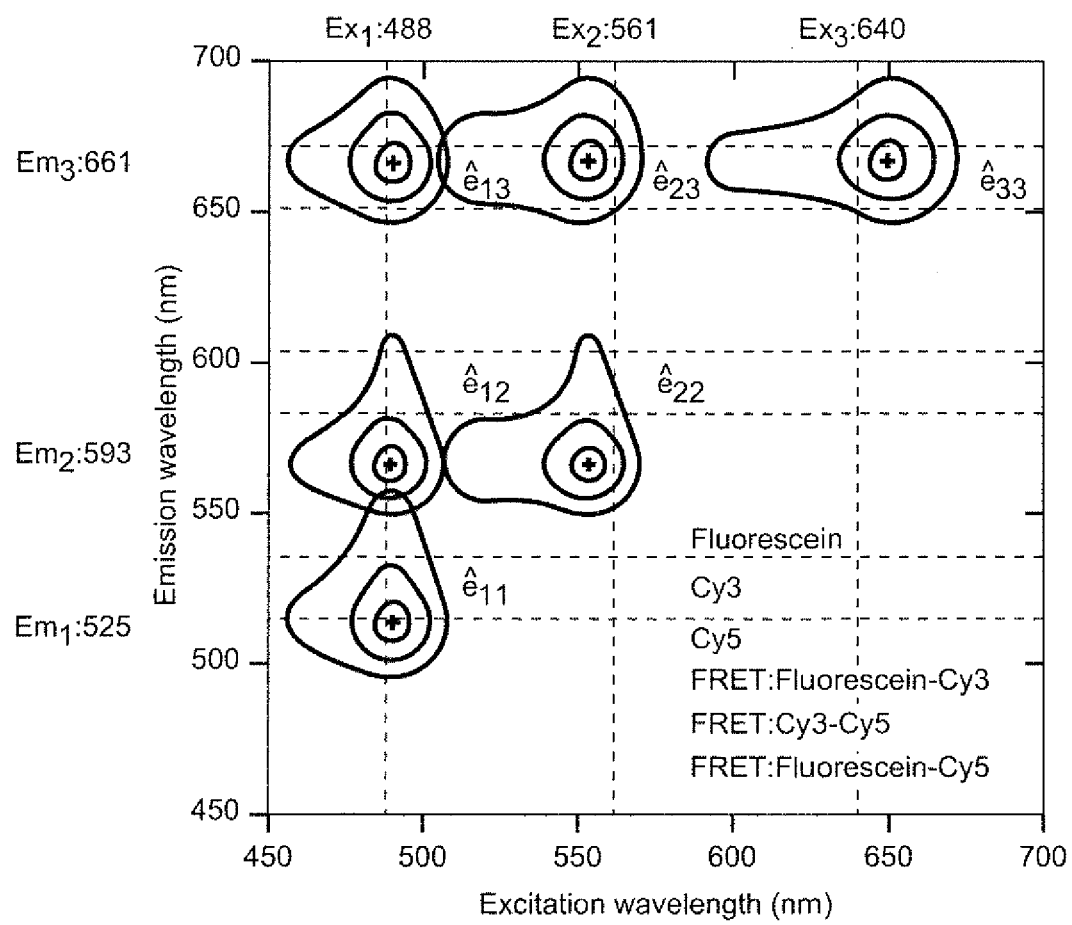

The time-resolved EEM analysis of multi-color FRET proceeds as illustrated in FIG. 10, using the three-color FRET case in FIG. 1 as the example. The color codes indicate the different fluorescence decay models for individual EEM channels. The process starts with the EEM channel that is the easiest to analyze, then progress to analyze more complex EEM channels using information obtained in previous steps.

(1) Determine the lifetime of Cy5 ($\tau_3$), the reddest fluorophore from a pure Cy5-labeled sample or, from the Cy5 EEM channel $\hat{e}_{33}$. The lifetime of Cy5 remains unchanged because Cy5 serves as acceptor in all FRET complexes.

(2) EEM channel $\hat{e}_{23}$ contains the signal generated by Cy3-Cy5 FRET. Channel $\hat{e}_{23}$ can be fitted with the one-step FRET model, Equation (6), with known acceptor lifetime $\tau_3$. The fitting yields $\tau_2^{123}$, the lifetime of Cy3 when it is quenched by Cy5

(3) EEM channel $\hat{e}_{22}$ contains fluorescence decays from both quenched and unquenched Cy3. A double exponential decay lifetime fitting with known lifetimes of quenched Cy3 $\tau_2^{123}$ (solved in Step 2) and unquenched Cy3 $\tau_{20}$ (measured from pure Cy3-labeled samples) can be used to obtain the percentage of quenched Cy3 ($P_2$). The percentage of quenched Cy3 measured in this channel is the ensemble average of all possible molecular forms that contains Cy3, i.e. all molecules containing Cy3-Cy5 vs. all molecules containing Cy3.

(4) EEM channel $\hat{e}_{12}$ contains FRET signals between fluorescein and Cy3, whose response is the product of the donor (quenched fluorescein) and acceptor (Cy3) responses. Two different molecular complexes, double labeled complexes fluorescein-Cy5 and triple-labeled complexes fluorescein-Cy3-Cy5, can both generate fluorescein-Cy3 FRET signal. Cy3 has different fluorescence lifetimes in these two kinds of complexes, a quenched lifetime $\tau_2^{123}$ in triple-labeled complexes, and an unquenched lifetime $\tau_{20}$ in double-labeled complexes. Thus in the FRET model, Equation (6), the acceptor (Cy3) response becomes a double-exponential decay with two lifetime components $\tau_2^{123}$ (solved in Step 2) and $\tau_{20}$ (measured from pure Cy3-labeled sample). The acceptor (Cy3) frequency response needed in Equation (6) for fitting channel $\hat{e}_{12}$ is identical to the response of the Cy3 EEM channel ($\hat{e}_{22}$), which is known. The only unknown in channel $\hat{e}_{12}$ is the decay of quenched donor (fluorescein). Fitting the response of channel $\hat{e}_{12}$ with Equation (6) yields the lifetime of quenched fluorescein $\tau_1^{123}$.

(5) EEM channel $\hat{e}_{11}$ contains fluorescence decays from quenched and unquenched fluorescein. A double exponential decay lifetime model with known lifetimes of quenched fluorescein $\tau_1^{123}$ (solved in Step 4) and unquenched fluorescein $\tau_{10}$ (measured from single labeled samples) obtains the percentage of quenched vs. all fluorescein.

(6) Finally EEM channel $\hat{e}_{13}$ contains signal from a two-step FRET process, (fluorescein to Cy3 then Cy3 to Cy5), and potentially signal from one-step FRET directly from fluorescein to Cy5. Multi-step FRET cascade signal only exists in multi-color FRET complex, and its frequency domain fluorescence lifetime response is a product of individual frequency domain lifetime responses of all fluorophores participating in the energy transfer chain. In the case of two-step FRET, the model is a product of frequency responses of three participating fluorophores (quenched fluorescein $\tau_1^{123}$, quenched Cy3 $\tau_2^{123}$ and final acceptor Cy5 $\tau_{30}$). The predicted signal is compared against the measured signal in channel $\hat{e}_{13}$. This step serves as verification on whether one-step FRET occurs between fluorescein and Cy5. If one-step FRET is present between fluorescein and Cy5, channel 13 will deviate from the two-step FRET model and will need to be analyzed as a mixture of two-step and one-step FRET processes.

The multi-step analysis procedure involves at most a single unknown lifetime parameter at each step, and is therefore more robust than direct multi-decay analysis. It requires time-resolved measurements on all EEM channels, which can only be obtained in parallel and in high speed by the FLEEM technique. It is uniquely developed for fast, robust analysis of multiplexed FRET based on results from the FLEEM imaging system.

The analysis method has been applied to the quantification of three-color FRET in incompletely hybridized triple-labeled DNA oligonucleotides. Quantitative measurements of the three-color FRET process in triple-labeled double-strand DNA were obtained in the presence of free single-labeled and double-labeled DNA. The results verified that this analysis method is valid for studying multi-color FRET between multiple macromolecules in biochemical equilibrium.

While the invention has been described above by reference to various embodiments, it will be understood that changes and modifications may be made without departing from the scope of the invention, which is to be defined only by the appended claims and their equivalents.

What is claimed is:

1. An apparatus for measuring time-resolved excitation-emission of a sample, comprising:
   an interferometer that includes an optical delay line;
   a multi-wavelength radiation source providing an input laser beam of radiation of multiple wavelengths to the interferometer, said interferometer providing an excitation radiation beam of said multiple wavelengths for scanning the sample and exciting fluorophores in the sample, said fluorophores emitting emission radiation beams in response to the excitation radiation beam;
   wherein said optical delay line comprises a rotating polygonal mirrored surface and optics that cause the input beam to impinge onto the polygonal mirrored surface at least four times, said polygonal mirrored surface reflecting said input beam to provide said excitation radiation beam, and wherein frequency-sweeping laser modulations from 0 to at least 10 MHz through interference in the excitation radiation beam are generated at an interference modulation frequency that is linear to the path-length scanning speed of the rotating polygonal mirrored surface;
   a mechanism scanning the excitation radiation beam across the sample;
   a plurality of modulation detectors detecting separately different wavelength components of said excitation radiation beam to provide excitation modulation signals;
   a plurality of emission detectors detecting separately different wavelength components of said emission radiation beam to acquire an image of the sample to provide emission signals; and
   an instrument analyzing the excitation modulation signals and the emission signals to determine with at least nanosecond resolution a time-resolved signal or signals of one or more excitation-emission photon pathways in the sample.

2. The apparatus of claim 1, wherein said optical delay line does not include any diffraction element.

3. The apparatus of claim 1, wherein said input beam emerges as an exit beam from said optical delay line after reflections by the polygonal mirrored surface, and said exit beam is substantially stationary so that there is no walk-off of the exit beam in said optical delay line.

4. The apparatus of claim 1, wherein said instrument comprises at least two RF mixers, each of said at least two mixers mixing one of the excitation modulation signals with emission signals provided in response to different wavelength components of said emission radiation beam, or mixing one of the emission signals with excitation modulation signals provided in response to different wavelength components of said excitation radiation beam.

5. The apparatus of claim 1, wherein said emission radiation beam includes at least two pairs of wavelength components, and the two wavelength components in each of the pairs are of the same wavelength but different polarizations, said instrument comprising a polarizing beam splitter that separates said wavelength components of said emission radiation beam of different polarizations.

6. The apparatus of claim 5, said instrument comprising at least two pairs of RF mixers, each of said at least two pairs of mixers mixing one of the emission signals provided in response to the wavelength component of the same polarization and wavelength of said emission radiation beam with excitation modulation signals provided in response to different wavelength components of said excitation radiation beam, or mixing one of the excitation modulation signals with emission signals provided in response to different wavelength components of the same polarization of said emission radiation beam.

7. The apparatus of claim 1, further comprising confocal optics that focus said excitation radiation beam to the sample.

8. The apparatus of claim 1, further comprising optics that focus said excitation radiation beam to the sample in a scanning-laser optical tomography configuration.

9. An apparatus for measuring a sample, comprising;
   optics that focus a radiation beam to the sample in a scanning-laser optical tomography configuration, said optics comprising a beam shaper that shapes said radiation beam into a Bessel beam that is focused to the sample;
   a transmission detector that detects radiation from the radiation beam that is transmitted through the sample; and
   at least one second detector that detects radiation from the sample along an optical path away from the direction of the radiation beam.

10. The apparatus of claim 9, wherein said radiation beam is of multiple wavelengths, said apparatus further comprising a device that provides said radiation beam, said device comprising:
    an interferometer that includes an optical delay line; and
    a multi-wavelength radiation source providing an input laser beam of radiation of multiple wavelengths to the interferometer, said interferometer providing said radiation beam of said multiple wavelengths for scanning the sample and exciting fluorophores in the sample, said fluorophores emitting an emission beam in response to the radiation beam, said emission beam detected by said at least one second detector;
    wherein said optical delay line comprises an element with a rotating polygonal mirrored surface and optics that cause the input beam to impinge onto the polygonal mirrored surface which reflects said input beam to provide said radiation beam, and wherein frequency-sweeping laser modulations through interference in the radiation beam are generated at an interference modulation frequency that is linear to path-length scanning speed of the rotating polygonal mirrored surface.

11. The apparatus of claim 1,
    said instrument comprising a plurality of RF mixers, each of the RF mixers mixing an excitation modulation signal provided in response to a detected wavelength component of said excitation radiation beam and an emission signal provided in response to a detected wavelength component of said emission radiation beam to provide a high frequency component and a low frequency component, said instrument further comprising a low pass filter attenuating the high frequency component and an analog to digital converter that digitizes said low frequency component.

12. The apparatus of claim 11, wherein said instrument introduces a timing offset and a consequent frequency shift between the detected excitation radiation beam signal and emission radiation beam wavelength component signals.

13. The apparatus of claim 11, wherein said low frequency component is in a frequency range of about 100 KHz to about 10 MHz.

14. A method for measuring time-resolved excitation-emission of a sample, comprising:
- providing an input laser beam of radiation of multiple wavelengths to an interferometer that includes an optical delay line, causing the interferometer to provide an excitation radiation beam of said multiple wavelengths, said optical delay line comprising a rotating polygonal mirrored surface;
- scanning the sample and exciting fluorophores in the sample using the excitation radiation beam, said fluorophores emitting an emission radiation beam in response to the excitation radiation beam;
- causing the input beam to impinge at least four times onto the polygonal mirrored surface which reflects said input beam to provide said excitation radiation beam, wherein frequency-sweeping laser modulations from about 0 to at least 10 MHz through interference in the excitation radiation beam are generated at an interference modulation frequency that is linear to the path-length scanning speed of the rotating polygonal mirrored surface;
- scanning the excitation radiation beam across the sample;
- detecting separately different wavelength components of said excitation radiation beam to provide excitation modulation signals;
- detecting separately different wavelength components of said emission radiation beam to acquire an image of the sample to provide emission signals; and
- analyzing the excitation modulation signals and emission signals to determine with at least nanosecond resolution a time-resolved signal or signals of one or more excitation-emission photon pathways in the sample,
- wherein said analyzing includes:
- mixing an excitation modulation signal provided in response to a detected wavelength component of said excitation radiation beam and an emission signal provided in response to a detected wavelength component of said emission radiation beam to provide a high frequency component and a low frequency component;
- attenuating or removing the high frequency component; and
- digitizing said low frequency component.

15. The method of claim 14, wherein said low frequency component is in a frequency range of about 100 KHz to about 10 MHz.

16. The method of claim 14, further comprising adjusting an optical path length difference between the detected excitation radiation beam and emission radiation beam wavelength components, or adjusting a relative time-delay between the excitation modulation signals and the emission signals, or adjusting both said optical path length difference and said relative time-delay, to select a timing offset between the excitation modulation signals and the emission signals, so that said low frequency component is in a frequency range of about 100 KHz to about 10 MHz.

* * * * *